US011584950B2

(12) United States Patent
Pollak et al.

(10) Patent No.: US 11,584,950 B2
(45) Date of Patent: *Feb. 21, 2023

(54) METHODS AND SYSTEMS FOR DETECTING ENTITIES IN A BIOLOGICAL SAMPLE

(71) Applicant: S.D. Sight Diagnostics Ltd., Tel Aviv (IL)

(72) Inventors: Joseph Joel Pollak, Neve Daniel (IL); Daniel Levner, Brookline, MA (US); Yonatan Bilu, Jerusalem (IL); Arnon Houri Yafin, Jerusalem (IL); Noam Yorav-Raphael, Tekoa (IL); Yuval Greenfield, Sunnyvale, CA (US)

(73) Assignee: S.D. Sight Diagnostics Ltd., Tel Aviv (IL)

(*) Notice: Subject to any disclaimer, the term of this patent is extended or adjusted under 35 U.S.C. 154(b) by 306 days.

This patent is subject to a terminal disclaimer.

(21) Appl. No.: 16/705,941

(22) Filed: Dec. 6, 2019

(65) Prior Publication Data
US 2020/0181680 A1   Jun. 11, 2020

Related U.S. Application Data

(63) Continuation of application No. 14/369,251, filed as application No. PCT/IL2012/050556 on Dec. 27, 2012, now Pat. No. 10,640,807.

(60) Provisional application No. 61/664,769, filed on Jun. 27, 2012.

(30) Foreign Application Priority Data

Dec. 29, 2011   (WO) .................. PCT/IL2011/000973

(51) Int. Cl.
*C12Q 1/68* (2018.01)
*G01N 1/30* (2006.01)

(52) U.S. Cl.
CPC .................. *C12Q 1/68* (2013.01); *G01N 1/30* (2013.01)

(58) Field of Classification Search
CPC .................................... C12Q 1/68; G01N 1/30
See application file for complete search history.

(56) References Cited

U.S. PATENT DOCUMENTS

| 3,603,156 | A | 9/1971 | Konkol |
| 3,676,076 | A | 7/1972 | Grady |
| 3,786,184 | A | 1/1974 | Pieters |
| 3,916,205 | A | 10/1975 | Kleinerman |
| 3,967,056 | A | 6/1976 | Yata et al. |
| 4,076,419 | A | 2/1978 | Kleker |
| 4,209,548 | A | 9/1980 | Bacus |
| 4,350,884 | A | 9/1982 | Dieter |
| 4,454,235 | A | 6/1984 | Johnson |
| 4,494,479 | A | 1/1985 | Drury et al. |
| 4,580,895 | A | 4/1986 | Patel |
| 4,700,298 | A | 10/1987 | Palcic et al. |
| 4,761,381 | A | 8/1988 | Blatt et al. |
| 4,774,192 | A | 9/1988 | Terminiello et al. |
| 4,803,352 | A | 2/1989 | Bierleutgeb |
| 4,849,430 | A | 7/1989 | Oberhardt |
| 4,851,330 | A | 7/1989 | Kohne |
| 4,902,101 | A | 2/1990 | Fujihara et al. |
| 5,001,067 | A | 3/1991 | Coleman et al. |
| 5,064,282 | A | 11/1991 | Curtis |
| 5,229,265 | A | 7/1993 | Tometsko |
| 5,300,779 | A | 4/1994 | Hillman et al. |
| 5,331,958 | A | 7/1994 | Oppenheimer |
| 5,430,542 | A | 7/1995 | Shepherd et al. |
| 5,470,751 | A | 11/1995 | Sakata et al. |
| 5,663,057 | A | 9/1997 | Drocourt et al. |
| 5,672,861 | A | 9/1997 | Fairley et al. |
| 5,674,457 | A | 10/1997 | Williamsson et al. |
| 5,745,804 | A | 4/1998 | Iwane |
| 5,782,770 | A | 7/1998 | Mooradian et al. |
| 5,827,190 | A | 10/1998 | Palcic et al. |
| 5,834,217 | A | 11/1998 | Levine et al. |
| 5,932,872 | A | 8/1999 | Price |
| 5,948,686 | A | 9/1999 | Wardlaw et al. |

(Continued)

FOREIGN PATENT DOCUMENTS

| CA | 2655024 | 1/2008 |
| CN | 101403650 | 6/2010 |

(Continued)

OTHER PUBLICATIONS

Second Office Action dated Jun. 3, 2021 which issued during the prosecution of Chinese Patent Application No. 2018113056094.
A Final Office Action dated Sep. 14, 2021 which issued during the prosecution of U.S. Appl. No. 16/106,085.
An International Search Report and Written Opinion for Application No. PCT/IB2020/061731 dated Feb. 22, 2021.
Invitation to pay fees and Partial Search Report issued for PCT Application No. PCT/IB2020/061732 dated Mar. 10, 2021.
Invitation to pay fees and Partial Search Report issued for PCT Application No. PCT/IB2020/061736 dated Mar. 12, 2021.
Invitation to pay fees and Partial Search Report issued for PCT Application No. PCT/IB2020/061728 dated Mar. 15, 2021.
International Search Report issued for PCT Application No. PCT/IB2020/061724 dated Mar. 18, 2021.

(Continued)

*Primary Examiner* — Blaine Lankford
(74) *Attorney, Agent, or Firm* — Sughrue Mion, PLLC

(57) ABSTRACT

Apparatus and methods for use with a blood sample are described. The blood sample is stained with Hoechst stain and Acridine Orange stain. A plurality of images of the blood sample are acquired. An object is identified as being a white blood cell candidate. A first stained area, which is stained by the Hoechst stain and which is disposed within the white blood cell candidate, is identified. A second stained area, which is stained by the Acridine Orange stain and which is disposed within the white blood cell candidate, is identified. A white blood cell is detected by determining that structural features of the stained areas satisfy predetermined criteria associated with a white blood cell. Other applications are also described.

5 Claims, 1 Drawing Sheet

(56) References Cited

U.S. PATENT DOCUMENTS

| | | |
|---|---|---|
| 5,985,595 A | 11/1999 | Krider et al. |
| 6,005,964 A | 12/1999 | Reid et al. |
| 6,027,695 A | 2/2000 | Oldenburg |
| 6,064,474 A | 5/2000 | Lee |
| 6,074,789 A | 6/2000 | Zelmanovic et al. |
| 6,101,104 A | 8/2000 | Yoon et al. |
| 6,262,798 B1 | 7/2001 | Shepherd et al. |
| 6,320,979 B1 | 11/2001 | Melen |
| 6,339,472 B1 | 1/2002 | Hafeman |
| 6,350,613 B1 | 2/2002 | Wardlaw et al. |
| 6,448,024 B1 | 9/2002 | Bruegger |
| 6,519,355 B2 | 2/2003 | Nelson |
| 6,554,788 B1 | 4/2003 | Hunley et al. |
| 6,582,964 B1 | 6/2003 | Samsoondar et al. |
| 6,611,777 B2 | 8/2003 | Samsoondar |
| 6,632,681 B1 | 10/2003 | Chu |
| 6,658,143 B2 | 12/2003 | Hansen |
| 6,664,528 B1 | 12/2003 | Cartlidge et al. |
| 6,711,516 B2 | 3/2004 | Samsoondar |
| 6,799,119 B1 | 9/2004 | Voorhees et al. |
| 6,819,408 B1 | 11/2004 | Scrivens et al. |
| 6,831,733 B2 | 12/2004 | Pettersson |
| 6,834,237 B2 | 12/2004 | Noergaard et al. |
| 6,836,559 B2 | 12/2004 | Abdel-fattah |
| 6,842,233 B2 | 1/2005 | Narisada |
| 6,866,823 B2 | 3/2005 | Wardlaw |
| 6,872,930 B2 | 3/2005 | Cartlidge et al. |
| 6,898,451 B2 | 5/2005 | Wuori |
| 6,903,323 B2 | 6/2005 | Cartlidge et al. |
| 6,929,953 B1 | 8/2005 | Wardlaw et al. |
| 6,949,384 B2 | 9/2005 | Samsoondar |
| 6,955,872 B2 | 10/2005 | Maples et al. |
| 6,956,650 B2 | 10/2005 | Boas |
| 6,989,891 B2 | 1/2006 | Braig et al. |
| 7,027,628 B1 | 4/2006 | Gagnon |
| 7,030,351 B2 | 4/2006 | Wasserman |
| 7,034,883 B1 | 4/2006 | Rosenqvist |
| 7,105,795 B2 | 9/2006 | Cartlidge et al. |
| 7,132,636 B1 | 11/2006 | Cartlidge |
| 7,133,547 B2 | 11/2006 | Marcelpoil |
| 7,151,246 B2 | 12/2006 | Fein et al. |
| 7,155,049 B2 | 12/2006 | Wetzel |
| 7,248,716 B2 | 7/2007 | Fein et al. |
| 7,274,810 B2 | 9/2007 | Reeves et al. |
| 7,283,217 B2 | 10/2007 | Ikeuchi |
| 7,288,751 B2 | 10/2007 | Cartlidge et al. |
| 7,305,109 B1 | 12/2007 | Gagnon |
| 7,324,694 B2 | 1/2008 | Chapoulaud |
| 7,329,537 B2 | 2/2008 | Qiu |
| 7,338,168 B2 | 3/2008 | Cartlidge et al. |
| 7,344,890 B2 | 3/2008 | Perez et al. |
| 7,346,205 B2 | 3/2008 | Walker, Jr. |
| 7,369,696 B2 | 5/2008 | Arini et al. |
| 7,411,680 B2 | 8/2008 | Chang |
| 7,417,213 B2 | 8/2008 | Krief et al. |
| 7,385,168 B2 | 9/2008 | Cartlidge et al. |
| 7,425,421 B2 | 9/2008 | Dertinger |
| 7,439,478 B2 | 10/2008 | Cartlidge et al. |
| 7,450,223 B2 | 11/2008 | Ikeuchi |
| 7,450,762 B2 | 11/2008 | Morell |
| 7,460,222 B2 | 12/2008 | Kalveram |
| 7,490,085 B2 | 2/2009 | Walker et al. |
| 7,493,219 B1 | 2/2009 | Qi |
| 7,580,120 B2 | 8/2009 | Hamada |
| 7,599,893 B2 | 10/2009 | Sapir |
| 7,601,938 B2 | 10/2009 | Cartlidge et al. |
| 7,602,954 B2 | 10/2009 | Marcelpoil |
| 7,605,356 B2 | 10/2009 | Krief |
| 7,609,369 B2 | 10/2009 | Simon-Lopez |
| 7,630,063 B2 | 12/2009 | Padmanabhan |
| 7,633,604 B2 | 12/2009 | Ikeuchi |
| 7,638,748 B2 | 12/2009 | Krief et al. |
| 7,663,738 B2 | 2/2010 | Johansson |
| 7,668,362 B2 | 2/2010 | Olson |
| 7,692,131 B2 | 4/2010 | Fein et al. |
| 7,697,764 B2 | 4/2010 | Kataoka |
| 7,702,181 B2 | 4/2010 | Gouch |
| 7,706,862 B2 | 4/2010 | Alfano et al. |
| 7,713,474 B2 | 5/2010 | Schulman et al. |
| 7,747,153 B2 | 6/2010 | Ibaraki |
| 7,765,069 B2 | 7/2010 | Ostoich |
| 7,777,869 B2 | 8/2010 | Nerin |
| 7,787,109 B2 | 8/2010 | Dosmann et al. |
| 7,796,797 B2 | 9/2010 | Nakaya et al. |
| 7,863,552 B2 | 1/2011 | Cartlidge et al. |
| 7,869,009 B2 | 1/2011 | Dosmann et al. |
| 7,894,047 B2 | 2/2011 | Hamada |
| 7,911,617 B2 | 3/2011 | Padmanabhan |
| 7,925,070 B2 | 4/2011 | Sumida |
| 7,929,121 B2 | 4/2011 | Wardlaw |
| 7,933,435 B2 | 4/2011 | Hunter |
| 7,936,913 B2 | 5/2011 | Nordell |
| 7,951,599 B2 | 5/2011 | Levine |
| 7,995,200 B2 | 8/2011 | Matsumoto |
| 7,998,435 B2 | 8/2011 | Reed et al. |
| 8,000,511 B2 | 8/2011 | Perz |
| 8,044,974 B2 | 10/2011 | Sumida |
| 8,045,782 B2 | 10/2011 | Li |
| 8,055,471 B2 | 11/2011 | Qi |
| 8,064,680 B2 | 11/2011 | Ramoser |
| 8,077,296 B2 | 12/2011 | Wardlaw |
| 8,081,303 B2 | 12/2011 | Levine |
| 8,105,554 B2 | 1/2012 | Kanigan et al. |
| 8,125,643 B2 | 2/2012 | Hansen |
| D655,421 S | 3/2012 | Lee et al. |
| 8,131,035 B2 | 3/2012 | Grady |
| 8,131,052 B2 | 3/2012 | Alexandrov |
| 8,150,114 B2 | 4/2012 | Svanberg |
| 8,154,713 B2 | 4/2012 | Simon-Lopez |
| 8,165,385 B2 | 4/2012 | Reeves |
| 8,175,353 B2 | 5/2012 | Westphal |
| 8,184,273 B2 | 5/2012 | Dosmann |
| 8,216,832 B2 | 7/2012 | Battrell et al. |
| 8,224,058 B2 | 7/2012 | Lindberg |
| 8,269,954 B2 | 9/2012 | Levine |
| 8,280,134 B2 | 10/2012 | Hoyt |
| 8,310,659 B2 | 11/2012 | Wardlaw |
| 8,320,655 B2 | 11/2012 | Sarachan |
| 8,331,642 B2 | 12/2012 | Zerfass |
| 8,339,586 B2 | 12/2012 | Zahniser |
| 8,345,227 B2 | 1/2013 | Zahniser |
| 8,351,676 B2 | 1/2013 | Dai |
| 8,363,221 B2 | 1/2013 | Hansen |
| 8,379,944 B2 | 2/2013 | Grady |
| 8,428,331 B2 | 4/2013 | Dimarzio |
| 8,432,392 B2 | 4/2013 | Kim |
| 8,477,294 B2 | 7/2013 | Zahniser |
| 8,481,303 B2 | 7/2013 | Faris et al. |
| 8,488,111 B2 | 7/2013 | Zahniser |
| 8,491,499 B2 | 7/2013 | Choi et al. |
| 8,526,704 B2 | 9/2013 | Dobbe |
| 8,570,496 B2 | 10/2013 | Chen |
| 8,582,924 B2 | 11/2013 | De La Torre-Bueno |
| 8,638,427 B2 | 1/2014 | Wardlaw |
| 8,712,142 B2 | 4/2014 | Rajpoot |
| 8,736,824 B2 | 5/2014 | Matsui |
| 8,744,165 B2 | 6/2014 | Liu |
| 8,778,687 B2 | 7/2014 | Levine |
| 8,792,693 B2 | 7/2014 | Satish |
| 8,837,803 B2 | 9/2014 | Wang et al. |
| 8,849,024 B2 | 9/2014 | Shinoda |
| 8,873,827 B2 | 10/2014 | Mcculloch |
| 8,877,458 B2 | 11/2014 | Maurer |
| 8,878,923 B2 | 11/2014 | Henderson |
| 8,885,154 B2 | 11/2014 | Wardlaw |
| 8,885,912 B2 | 11/2014 | Sui |
| 8,891,851 B2 | 11/2014 | Spaulding |
| 8,922,761 B2 | 12/2014 | Zahniser |
| 8,942,458 B2 | 1/2015 | Takahashi |
| 8,964,171 B2 | 2/2015 | Zahniser |
| 8,994,930 B2 | 3/2015 | Levine |
| 9,012,868 B2 | 4/2015 | Courtney et al. |
| 9,041,792 B2 | 5/2015 | Van Leeuwen |
| 9,050,595 B2 | 6/2015 | Miller et al. |

(56) References Cited

U.S. PATENT DOCUMENTS

| | | | |
|---|---|---|---|
| 9,064,301 B2 | 6/2015 | Xie et al. |
| 9,046,473 B2 | 9/2015 | Levine |
| 9,176,121 B2 | 11/2015 | Winkelman et al. |
| 9,186,843 B2 | 11/2015 | Chan et al. |
| 9,240,043 B2 | 1/2016 | Christiansen |
| 9,322,767 B2 | 4/2016 | Ehrenkranz |
| 9,329,129 B2 | 5/2016 | Pollak et al. |
| 9,342,734 B2 | 5/2016 | Lin et al. |
| 9,404,852 B2 | 8/2016 | Braig et al. |
| 9,470,609 B2 | 10/2016 | Wimberger-friedl |
| 9,477,875 B2 | 10/2016 | Ohya |
| 9,522,396 B2 | 12/2016 | Bachelet |
| 9,588,033 B2 | 3/2017 | Zahniser et al. |
| 9,767,343 B1 | 9/2017 | Jones et al. |
| 9,820,990 B2 | 11/2017 | Pak et al. |
| 9,934,571 B2 | 4/2018 | Ozaki |
| 10,024,858 B2 | 7/2018 | Smith et al. |
| 10,061,972 B2 | 8/2018 | Champlin |
| 10,093,957 B2 | 10/2018 | Pollak et al. |
| 10,169,861 B2 | 1/2019 | Ozaki et al. |
| 10,176,565 B2 | 1/2019 | Greenfield |
| 10,281,386 B2 | 5/2019 | Hsu et al. |
| 10,488,644 B2 | 11/2019 | Eshel et al. |
| 10,640,807 B2* | 5/2020 | Pollak ..................... G01N 1/30 |
| 2002/0009711 A1 | 1/2002 | Wada et al. |
| 2002/0028158 A1 | 3/2002 | Wardlaw et al. |
| 2002/0028471 A1 | 3/2002 | Oberhardt |
| 2003/0017085 A1 | 3/2003 | Kercso et al. |
| 2003/0161514 A1 | 8/2003 | Curry |
| 2003/0170613 A1 | 9/2003 | Straus |
| 2003/0197925 A1 | 10/2003 | Hamborg |
| 2003/0224522 A1 | 12/2003 | de Jong |
| 2003/0227612 A1 | 12/2003 | Fein et al. |
| 2003/0227673 A1 | 12/2003 | Nakagawa |
| 2003/0231791 A1 | 12/2003 | Torre-Bueno et al. |
| 2004/0240050 A1 | 2/2004 | Ogihara |
| 2004/0241677 A1 | 2/2004 | Lin et al. |
| 2004/0132171 A1 | 7/2004 | Rule et al. |
| 2004/0170312 A1 | 9/2004 | Soenksen |
| 2004/0185447 A1 | 9/2004 | Maples et al. |
| 2004/0218804 A1 | 11/2004 | Affleck et al. |
| 2005/0089208 A1 | 4/2005 | Dong et al. |
| 2005/0109959 A1 | 5/2005 | Wasserman et al. |
| 2005/0175992 A1 | 8/2005 | Aberl et al. |
| 2005/0286800 A1 | 12/2005 | Gouch |
| 2006/0003458 A1 | 1/2006 | Golovchenko et al. |
| 2006/0045505 A1 | 3/2006 | Zeineh |
| 2006/0063185 A1 | 3/2006 | Vannier |
| 2006/0187442 A1 | 8/2006 | Chang et al. |
| 2006/0190226 A1 | 8/2006 | Jojic et al. |
| 2006/0222567 A1 | 10/2006 | Kloepfer et al. |
| 2006/0223052 A1 | 10/2006 | MacDonald et al. |
| 2006/0223165 A1 | 10/2006 | Chang et al. |
| 2007/0252984 A1 | 1/2007 | Van Beek et al. |
| 2007/0054350 A1 | 3/2007 | Walker, Jr. |
| 2007/0117158 A1 | 5/2007 | Coumans et al. |
| 2007/0243117 A1 | 10/2007 | Wardlaw et al. |
| 2007/0250301 A1 | 10/2007 | Vaisberg et al. |
| 2008/0020128 A1 | 1/2008 | van Ryper |
| 2008/0059135 A1 | 3/2008 | Murugkar et al. |
| 2008/0118399 A1 | 5/2008 | Fleming |
| 2008/0187466 A1 | 8/2008 | Wardlaw et al. |
| 2008/0212069 A1 | 9/2008 | Goldberg et al. |
| 2008/0260369 A1 | 10/2008 | Ibaraki |
| 2008/0273776 A1 | 11/2008 | Krief et al. |
| 2008/0305514 A1 | 12/2008 | Alford et al. |
| 2009/0066934 A1 | 3/2009 | Gao et al. |
| 2009/0075324 A1 | 3/2009 | Pettersson |
| 2009/0128618 A1 | 5/2009 | Fahn et al. |
| 2009/0185734 A1 | 7/2009 | Lindberg et al. |
| 2009/0191098 A1 | 7/2009 | Beard et al. |
| 2009/0195688 A1 | 8/2009 | Henderson et al. |
| 2009/0213214 A1 | 8/2009 | Yamada |
| 2009/0258347 A1 | 10/2009 | Scott |
| 2009/0269799 A1 | 10/2009 | Winkelman et al. |
| 2009/0291854 A1 | 11/2009 | Wiesinger-Mayr et al. |
| 2010/0068747 A1 | 3/2010 | Herrenknecht |
| 2010/0104169 A1 | 4/2010 | Yamada |
| 2010/0112631 A1 | 5/2010 | Hur et al. |
| 2010/0120129 A1 | 5/2010 | Amshey et al. |
| 2010/0136556 A1 | 6/2010 | Friedberger et al. |
| 2010/0136570 A1 | 6/2010 | Goldberg et al. |
| 2010/0152054 A1 | 6/2010 | Love |
| 2010/0157086 A1 | 6/2010 | Segale et al. |
| 2010/0172020 A1 | 7/2010 | Price |
| 2010/0234703 A1 | 9/2010 | Sterling et al. |
| 2010/0254596 A1 | 10/2010 | Xiong |
| 2010/0256323 A1 | 10/2010 | Perz |
| 2010/0256918 A1 | 10/2010 | Chen et al. |
| 2010/0295998 A1 | 11/2010 | Sakai et al. |
| 2010/0300563 A1 | 12/2010 | Ramunas et al. |
| 2011/0009163 A1 | 1/2011 | Fletcher |
| 2011/0030458 A1 | 2/2011 | Park et al. |
| 2011/0102571 A1 | 5/2011 | Yoneyama |
| 2011/0123398 A1 | 5/2011 | Carrhilo et al. |
| 2011/0144480 A1 | 6/2011 | Lu et al. |
| 2011/0149097 A1 | 6/2011 | Danuser et al. |
| 2011/0151502 A1 | 6/2011 | Kendall et al. |
| 2011/0178716 A1 | 7/2011 | Krockenberger et al. |
| 2011/0212486 A1 | 9/2011 | Yamada |
| 2011/0249910 A1 | 10/2011 | Henderson |
| 2011/0275111 A1 | 11/2011 | Pettigrew et al. |
| 2012/0002195 A1 | 1/2012 | Wu et al. |
| 2012/0021951 A1 | 1/2012 | Hess et al. |
| 2012/0030618 A1 | 2/2012 | Leong et al. |
| 2012/0044342 A1 | 2/2012 | Hing et al. |
| 2012/0058504 A1 | 3/2012 | Li et al. |
| 2012/0092477 A1 | 4/2012 | Kawano et al. |
| 2012/0120221 A1 | 5/2012 | Dong et al. |
| 2012/0169863 A1 | 7/2012 | Bachelet et al. |
| 2012/0225446 A1 | 9/2012 | Wimberger-Friedl et al. |
| 2012/0312957 A1 | 12/2012 | Loney et al. |
| 2012/0320045 A1 | 12/2012 | Yao |
| 2013/0023007 A1 | 1/2013 | Zahniser et al. |
| 2013/0078668 A1 | 3/2013 | Levine et al. |
| 2013/0130262 A1 | 5/2013 | Battrell et al. |
| 2013/0170730 A1 | 7/2013 | Yu et al. |
| 2013/0176551 A1 | 7/2013 | Wardlaw et al. |
| 2013/0273968 A1 | 10/2013 | Rhoads et al. |
| 2013/0284924 A1 | 10/2013 | Mizuochi et al. |
| 2013/0290225 A1 | 10/2013 | Kamath et al. |
| 2014/0139625 A1 | 5/2014 | Mathuis et al. |
| 2014/0139630 A1 | 5/2014 | Kowalevicz |
| 2014/0186859 A1 | 7/2014 | Calderwood et al. |
| 2014/0205176 A1 | 7/2014 | Obrien et al. |
| 2014/0347459 A1 | 11/2014 | Greenfield et al. |
| 2015/0037806 A1 | 2/2015 | Pollak et al. |
| 2015/0124082 A1 | 5/2015 | Kato et al. |
| 2015/0190063 A1 | 7/2015 | Zakharov et al. |
| 2015/0278575 A1 | 10/2015 | Allano et al. |
| 2015/0302237 A1 | 10/2015 | Ohya et al. |
| 2015/0316477 A1 | 11/2015 | Pollak et al. |
| 2016/0208306 A1 | 7/2016 | Pollak et al. |
| 2016/0246046 A1 | 8/2016 | Yorav-Raphael et al. |
| 2016/0279633 A1 | 9/2016 | Bachelet et al. |
| 2017/0052110 A1 | 2/2017 | Malissek et al. |
| 2017/0160185 A1 | 6/2017 | Minemura et al. |
| 2017/0218425 A1 | 8/2017 | Chen et al. |
| 2017/0307496 A1 | 10/2017 | Zahniser et al. |
| 2017/0328924 A1 | 11/2017 | Jones et al. |
| 2018/0246313 A1 | 8/2018 | Eshel et al. |
| 2018/0296102 A1 | 10/2018 | Satish et al. |
| 2019/0002950 A1 | 1/2019 | Pollak et al. |
| 2019/0347467 A1 | 11/2019 | Ohsaka et al. |

FOREIGN PATENT DOCUMENTS

| | | |
|---|---|---|
| CN | 102387864 A | 3/2012 |
| EP | 0073551 | 3/1983 |
| EP | 479231 | 4/1992 |
| EP | 1381229 | 1/2003 |
| EP | 1698883 | 9/2006 |
| EP | 2145684 | 1/2010 |
| EP | 3001174 | 3/2016 |

(56) References Cited

FOREIGN PATENT DOCUMENTS

| | | |
|---|---|---|
| EP | 3 123 927 A1 | 2/2017 |
| EP | 2211165 B1 | 7/2017 |
| EP | 3482189 A1 | 5/2019 |
| EP | 1 873 232 B1 | 2/2020 |
| GB | 2329014 | 3/1999 |
| JP | 61198204 | 9/1986 |
| JP | H11-73903 | 3/1999 |
| JP | 2000/199845 | 7/2000 |
| JP | 2004-144526 | 5/2004 |
| JP | 2004-257768 | 9/2004 |
| JP | 2006-301270 | 11/2006 |
| JP | 2007-040814 | 2/2007 |
| JP | 2017-209530 A | 11/2017 |
| WO | 1985/005446 | 12/1985 |
| WO | 1996/001438 | 1/1996 |
| WO | 1996/012981 | 5/1996 |
| WO | 1996/013615 | 5/1996 |
| WO | 2000/006765 | 2/2000 |
| WO | 2000/052195 | 8/2000 |
| WO | 2000/055572 | 9/2000 |
| WO | 2002/033400 | 4/2002 |
| WO | 2003/081525 | 2/2003 |
| WO | 2003/056327 | 7/2003 |
| WO | 2003/073365 | 9/2003 |
| WO | 2004/111610 | 12/2004 |
| WO | 2005/121863 | 12/2005 |
| WO | 2006/121266 | 11/2006 |
| WO | 2008/063135 | 5/2008 |
| WO | 2010/056740 | 5/2010 |
| WO | 2010/116341 | 10/2010 |
| WO | 2010/126903 | 11/2010 |
| WO | 2011/076413 | 6/2011 |
| WO | 2011/123070 | 10/2011 |
| WO | 2011/143075 | 11/2011 |
| WO | 2012/000102 | 1/2012 |
| WO | 2012/030313 | 3/2012 |
| WO | 2012/090198 | 5/2012 |
| WO | 2012/154333 | 11/2012 |
| WO | 2013/041951 A1 | 3/2013 |
| WO | 2013/098821 | 7/2013 |
| WO | 2014/159620 | 10/2014 |
| WO | 2014188405 A1 | 11/2014 |
| WO | 2015/001553 | 1/2015 |
| WO | 2015/029032 | 3/2015 |
| WO | 2016/030897 | 3/2016 |
| WO | 2017/195208 | 11/2016 |
| WO | 2017/046799 | 3/2017 |
| WO | 2017/168411 | 10/2017 |
| WO | 2017/195205 | 11/2017 |
| WO | 2019035084 A1 | 2/2019 |
| WO | 2019/097387 | 5/2019 |
| WO | 2019102277 A1 | 5/2019 |
| WO | 2019198094 A1 | 10/2019 |
| WO | 2021/079305 A1 | 4/2021 |
| WO | 2021/079306 A1 | 4/2021 |

OTHER PUBLICATIONS

An International Search Report and Written Opinion for PCT Application No. PCT/IB2020/061732 dated May 7, 2021.
International Search Report and Written Opinion for PCT Application No. PCT/IB2020/061728 dated May 7, 2021.
International Search Report and Written Opinion for PCT Application No. PCT/IB2020/061736 dated May 3, 2021.
An International Search Report dated Jul. 27, 2012, in International Application No. PCT/IL2011/000973.
Communication dated Jun. 15, 2018 from the United States Patent and Trademark Office in U.S. Appl. No. 14/369,251.
Communication dated Jun. 29, 2018 from the United States Patent and Trademark Office in U.S. Appl. No. 15/174,490.
Communication dated Mar. 2, 2017, from the United States Patent and Trademark Office in U.S. Appl. No. 14/369,251.
Knesel, "Roche Image Analysis Systems, Inc.", Acta Cytologica, vol. 40, 1996, pp. 60-66, ( 7 pages total).
Leif, "Methods for Preparing Sorted Cells as Monolayer Specimens", Springer Lab Manuals, Section 7—Chapter, 2000, 5 pp. 592-619. ( 28 pages total).
Life Technologies Corporation, "Counting blood cells with Countless Automated Cell Counter" found at http://www.lifetechnologies.com/content/dam/LifeTech/migration/files/cell-tissue-analysis/pdfs.par.83996.file.dat/w-082149-countless-application-blood-cells.pdf, 2009, ( 4 pages total).
Moody , "Rapid Diagnostic Tests for Malaria Parasites", Clinical Microbiology Reviews, vol. 15, No. 1, 2002, pp. 66-78, (13 pages total).
Zahniser et al., Automated Slide Preparation System for the Clinical Laboratory, Cytometry, 1996 Vol. 26, No. 10, pp. 60-64, (5 pages total).
Communication dated Dec. 21, 2018, from the United States Patent and Trademark Office in U.S. Appl. No. 14/369,251.
"Blood specimens:Microscopic Examination", Centers for Disease Control and Prevention CDC, Diagnostic Procedures, 2009, <http://www.dpd.cdc.gov/dpdx/HTML/Frames/DiagnosticProcedures/body_dp_bloodexamin.htm>, (2 Pages total).
Merchant et al. , "Computer-Assisted Microscopy", The essential guide to image processing, Chapter 27, 2009, Academic Press, pp. 777-831 ( 55 pages total).
Saraswat, et al. "Automated microscopic image analysis for leukocytes identification: A survey", ABV-Indian Institute of Information Technology and Management, Gwalior, India, Micron, 2014, vol. 65, pp. 20-33.
Hiremath, P.S,. et al., "Automated Identification and Classification of White Blood Cells (Leukocytes) in Digital Microscopic Images", IJCA Special Issue on "Recent Trends in Image Processing and Pattern Recognition" RTIPPR, 2010, pp. 59-63.
Witt, et al. "Establishing traceability of photometric absorbance values for accurate measurements of the haemoglobin concentration in blood.", Metrologia 50 (2013) 539-548.
Putzu, et al., "Leucocyte classification for leukaemia detection using image processing techniques.", Artificial Intelligence in Medicine, vol. 63, No. 3, Nov. 1, 2014, pp. 1-31.
Varga, et al., "An automated scoring procedure for the micronucleus test by image analysis", Mutagenesis vol. 19 No. 5 pp. 391-397, 2004.
Ran, Qiong et al. "Spatial-spectral blood cell classification with microscopic hyperspectral imagery", Proc. SPIE 10461, AOPC 2017: Optical Spectroscopy and Imaging, 1046102 (Oct. 24, 2017) (12 pages total).
Omucheni et al. "Application of principal component analysis to multispectral-multimodal optical image analysis for malaria diagnostics", Malaria Journal 2014, 13:485 http://www.malariajournal.com/content/13/1/485 (11 pages total).
Ben-Suliman—2018—"Computerized Counting-Based System for Acute Lymphoblastic Leukemia Detection in Microscopic Blood Images" 27th International Conference on Artificial Neural Networks, Rhodes, Greece, Oct. 4-7, 2018, Proceedings, Part II, pp. 167-178.
International Search Report issued for PCT Application No. PCT/IB2020/059924 dated Mar. 22, 2021.
International Search Report issued for PCT Application No. PCT/IB2020/059925 dated Mar. 26, 2021.
Invitation to pay fees and Partial Search Report issued for PCT Application No. PCT/IB2020/059924 dated Jan. 28, 2021.
Invitation to pay fees and Partial Search Report issued for PCT Application No. PCT/IB2020/059925 dated Feb. 4, 2021.
A European Examination Report dated Mar. 17, 2021. which issued during the prosecution of Application No. 14741677.0.
A Hearing Notice issued for Indian Application No. 4263/DELNP/2014 on Jan. 11, 2021.
An Office Action dated Mar. 2, 2021 for U.S. Appl. No. 16/106,085.
Agero, U., Mesquita, L.G., Neves, B.R.A., Gazzinelli, R.T. and Mesquita, O.N., 2004. Defocusing microscopy. Microscopy research and technique, 65(3), pp. 159-165.
Ahirwar, Neetu et al., "Advanced Image Analysis Based System for Automatic Detection and Classification of Malarial Parasite in Blood Images," International Journal of Information Technology

(56) References Cited

OTHER PUBLICATIONS and Knowledge Management Jan.-Jun. 2012, vol. 5, No. 1, pp. 59-64, Serial Publications Pvt. Ltd, India.
Anand, A., et al. "Automatic Identification of Malaria-Infected RBC with Digital Holographic Microscopy Using Correlation Algorithms." Photonics Journal, IEEE 4.5 (2012): 1456-1464.
Bacus, J.W., 1985. Cytometric approaches to red blood cells. Pure and Applied AL Chemistry, 57(4), pp. 593-598.
Biéler, Sylvain et al. "Improved detection of Trypanosoma brucei by lysis of red blood cells, concentration and LED fluorescence microscopy"; Acta Tropica; vol. 121, Issue 2, Feb. 2012, pp. 135-140.
Bovik, Alan C., et. "The Essential Guide to Image Processing", Chapter 27, "Computer Assisted Microscopy",pp. 777-831; Academic Press, 2009.
Bravo-Zanoguera, M.E., Laris, C.A., Nguyen, L.K., Oliva, M. and Price, J.H., 2007. Dynamic autofocus for continuous-scanning time-delay-and-integration image acquisition in automated microscopy. Journal of biomedical optics, 12(3), pp. 034011-034011.
Brenner et al., An Automated Microscope for Cytologic Research a Preliminary Evaluation, [The Journal of Histochecmistry and Cytochemistry, vol. 24, No. 1, pp. 100-111, 1976.
Briggs, C., et al., "Continuing developments with the automated platelet count", Blackwell Publishing Ltd, International Journal of Laboratory Hematology, Jan. 18, 2007, pp. 77-91, vol. 29 (15 pages total).
Centers for Disease Control and Prevention. DPDx—Laboratory Identification of Parasitic Diseases of Public Health Concern <http://www.cdc.gov/dpdx/diagnosticProcedures/blood/microexam.html>, Nov. 29, 2013.
Cervantes, Serena, Jacques Prudhomme, David Carter, Krishna G Gopi, Qian Li, Young-Tae Chang, and Karine G Le Roch, High-content live cell imaging with RNA probes: advancements in high-throughput antimalarial drug discovery, BMC Cell Biology 2009, 10:45, https://bmcmolcellbiol.biomedcentral.com/track/pdf/10.1186/1471-2121 -10-45 (Jun. 10, 2009).
Chiodini, P.L. et al., "Rapid diagnosis of malaria by fluorescence microscopy"; The Lancet, vol. 337, Issue 8741, P624-625, Mar. 9, 1991.
Chong, Shau Poh, Shilpa Pant, and Nanguang Chen. "Line-scan Focal Modulation Microscopy for Rapid Imaging of Thick Biological Specimens." SPIE/OSA/IEEE Asia Communications and Photonics. International Society f or Optics and Photonics, 2011.
Emma Eriksson et al: "Automated focusing of nuclei for time lapse experiments on single cells using holographic optical tweezers", Optics Express, vol. 17, No. 7, Mar. 24, 2009, pp. 5585-5594.
F. Boray Tek et al. "Parasite detection and identification for automated thin blood film malaria diagnosis" Computer Vision and Image Understanding vol. 114, Issue 1, Jan. 2010, pp. 21-32.
Fohlen-Walter, Anne PhD, et al., "Laboratory Identification of Cryoglobulinemia From Automated Blood Cell Counts, Fresh Blood Samples, and Blood Films", American Society for Clinical Pathology, Am J Clin Pathol, 2002, pp. 606-614, vol. 117 (9 pages total).
Frean, John. "Microscopic Determination of Malaria Parasite Load: Role of Image Analysis." Microscopy: Science, technology, Applications, and Education (2010): 862-866.
Gallo, V., Skorokhod, O.A., Schwarzer, e, and Arese, P. "Simultaneous determination of phagocytosis of Plasmodium falciparum-parasitized and non-parasitized red blood cells by flow cytometry"; Malaria Journal 2012 11:428.
Garcia, et al. "Laboratory Diagnosis of Blood-borne Parasitic Diseases; Approved Guideline"; NCCLS Documents M115-a, Jun. 2000.
Gordon, Andrew et al. "Single-cell quantification of molecules" Nature Methods 4, Jan. 21, 2007, pp. 175-181.
Gordon, Andrew et al. Supplementary Note to Gordon et al.: "Single-cell quantification of molecules" Nature Methods, Jan. 21, 2007, pp. 1-35.
Groen, F.C.A., et al. "A comparison of different focus functions for use in autofocus algorithms", Cytometry, Alan Liss, New York, US vol. 6, No. 2, Mar. 1, 1985 (Mar. 1, 1985) pp. 81-91.

Guy, Rebecca, Paul Liu, Peter Pennefather and Ian Crandall, "The use of fluorescence enhancement to improve the microscopic diagnosis of falciparum malaria", Malaria Journal 2007 6:89, https://malariajournal.biomedcentral.com/articles/10.1186/1475-2875-6-89, (Jul. 9, 2007).
Houri-Yafin, A., et al. "An enhanced computer vision platform for clinical diagnosis of malaria" Malaria Control and Elimination, 2016, p. 138, Vo. 5, Issue 1, omics International, India.
Jager et al. "Five-minute Giemsa stain for rapid dedtection of malaria parasites in blood smears", Tropical Doctor, Vo. 41, pp. 33-35, Jan. 2011.
Jahanmehr,S A H et al., "Simple Technique for Fluorescence Staining of Blood Cells with Acridine Orange", Journal of Clinical Pathology, Feb. 12, 1987, pp. 926-929 (4 pages total).
Joanny, Fanny, Helda Jana, and Benjamin Mordmllera, "In Vitro Activity of Fluorescent Dyes against Asexual Blood Stages of Plasmodium falciparum" DOI: 10.1128/AAC.00709-12.
Kawamoto, F. and P.F.Billingsley, "Rapid diagnosis of malaria by fluorescence microscopy", Parasitology Today, 8.2 (1992): 69-71.
Kawamoto,F. "Rapid diagnosis of malaria by fluorescence microscopy with light microscope and interference filter", The Lancet, vol. 337, pp. 200-202, Jan. 26, 1991.
Keiser, J. et al., "Acridine Orange for malaria diagnosis: its diagnostic performance, its promotion and implementation in Tanzania, and the implications for malaria control", Annals of Tropical Medicine and parasitology, 96.7 (2002): 643-654.
Kumar, Amit et al. "Enhanced Identification of Malarial Infected Objects using Otsu Algorithm from Thin Smear Digital Images." International Journal of Latest Research in Science and Technology vol. 1,Issue 2: pp. 159-163, Jul.-Aug. 2012).
Laboratory diagnosis of blood-borne parasitic diseases: approved guideline, 2000—NCCLS.
Le, Minh-Tam et al., "A novel semi-automatic image processing approach to determine Plasmodium falciparum parasitemia in Giemsa-stained thin blood smears", BMC Cell Biology, published Mar. 28, 2008.
Matcher, S.J., et al. "Use of the water absorption spectrum to quantify tissue chromophore concentration changes in near-infrared spectroscopy", Physics in Medicine & Biology, vol. 39, No. 1, 1994 pp. 177-196, IOP Publishing Ltd., UK.
Mendiratta, D.K et al. Evaluation of different methods for diagnosis of P. falciparum malaria; Indian J Med Microbiol. Jan. 2006;24(1):49-51.
Moon S, Lee S, Kim H, Freitas-Junior LH, Kang M, Ayong L, et al. (2013) An Image Analysis Algorithm for Malaria Parasite Stage Classification and Viability Quantification. PLoS One 8(4): e61812. https://doi.org/10.1371/journal.pone.0061812.
Ortyn, William E., et al. "Extended Depth of Field Imaging for High Speed Cell Analysis." Cytometry Part A 71.4, 2007): 215-231.
Osibote, O. A., et al. "Automated focusing in bright-field microscopy for tuberculosis detection", Journal of Microscopy 240.2 (2010)pp. 155-163.
Parasight LTD, WO2012/090198 A3, WIPO International Publication, "An Apparatus and Method for Automatic Detection of Pathogens," published Nov. 15, 2012, including International Search Report dated Jul. 27, 2012.
Pasini, Erica M. et al. "A novel live-dead staining methodology to study malaria parasite viability"; Malaria Journal 2013 12:190.
Piruska, Aigars et al., "The autofluorescence of plastic materials and chips measured under laser irradiation" Lab on a Chip, 2005, 5, 1348-1354, published Nov. 1, 2005.
Poon et al., "Automated Image Detection and Segmentation in Blood Smears", [Cytometry 1992 13:766-774].
Price Jeffrey H. and David A. Gough, "Comparison of phase-contrast and fluorescence digital autofocus for scanning microscopy", Cytometry 16.4 (1994) 283-297.
Purwar, Yashasvi, et al. "Automated and Unsupervised Detection of Malarial Parasites in Microscopic Images." Malaria Journal 10.1 (2011): 364.
Rappaz, Benjamin et al., "Comparative study of human erythrocytes by digital holographic microscopy, confocal microscopy, and impedance volume analyzer" Cytometry Part A, 2008, vol. 73, Issue 10, pp. 895-903, John Wiley & Sons, US.

(56) References Cited

OTHER PUBLICATIONS

Roma, P. M. S., et al. "Total three-dimensional imaging of phase objects using defocusing microscopy: Application to red blood cells." Applied Physics Letters 104,25 (2014): 251107.
Ross, Nicholas E., et al., "Automated image processing method for the diagnosis and classification of malaria on thin blood smears", Medical and Biological Engineering and Computing, May 2006, vol. 44, Issue 5, pp. 427-436, Springer Publishing Company, US.
Sheikh, H., Bin Zhu, Micheli-Tzanakou, E. (1996) "Blood cell identification using neural networks." Proceedings of the IEEE 22nd Annual Northeast Bioengineering Conference; pp. 119-120.
Shen, Feimo, Louis Hodgson and Klaus Hahn, "Digital autofocus method for automated microscopy", Methods in Enzymology vol. 414, 2006, pp. 620-632.
Shute G. T. and T. M. Sodeman, "Identification of malaria parasites by fluorescence microscopy and acridine orange staining", Bulletin of the World Health Organ. 1973; 48(5): 591-596.
Sun, Yu, S. Duthalerand B.J. Nelson, "Autofocusing algorithm selection in computer microscopy", 2005 IEEE/RSJ International Conference on Intelligent Robots and Systems.
Tek, F. Boray, Andrew G. Dempster, and Izzet Kale. "Computer Vision for Microscopy Diagnosis of Malaria." Malaria Journal 8.1 (2009): 153.
Thung, Ferdian, and Iping Supriana Suwardi. "Blood Parasite Identification Using Feature Based Recognition." Electrical Engineering and Informatics (ICEEI), 2011 International Conference on. IEEE, 2011.
Wissing, Frank et al. "Illumination of the Malaria Parasite Plasmodium falciparum Alters Intracellular pH", Implications for Live Cell Imaging; published Jul. 24, 2002,JBS Papers in Press, vol. 277 No. 40, pp. 27747-37755.
Wright, J H. "A Rapid Method for the Differential Staining of Blood Films and Malarial Parasites" Journal of medical research vol. 7,1 (1902): 138-44.
Wu, Caicai et al., "Feasibility study of the spectroscopic measurement of oxyhemoglobin using whole blood without pre-treatment", The Analyst, Mar. 1998, pp. 477-481, vol. 123 (5 pages total).
Wu, Qiang, Fatima Mechant, and Kenneth Castleman. Microscope Image Processing. Chapter 16, Autofocusing, pp. 441-467, Academic Press, 2010.
Xu, Lili, Asok Chaudhuri, "Plasmodium yoelii: A differential fluorescent technique using Acridine Orange to identify infected erythrocytes and reticulocytes in Duffy knockout mouse", Experimental Parasitology, vol. 110, Issue 1, May 2005, pp. 80-87, https://www.sciencedirect.com/science/article/pii/S001448940500038X, (May 31, 2005).
Yang, Ming, and Li Luo. "A Rapid Auto-Focus Method in Automatic Microscope." Signal Processing, 2008. ICSP 2008. 9th International Conference on IEEE,2008.
Yao, LN et al. "Pathogen identification and clinical diagnosis for one case infected with Babesia". Zhongguo ji sheng chong xue yu ji sheng chong bing za zhi Chinese journal of parasitology parasitic diseases, Aug. 2012.
Yazdanfar, S., Kenny, K.B., Tasimi, K., Corwin, A.D., Dixon, E.L. and Filkins, R.J., 2008. Simple and robust image-based autofocusing for digital microscopy. Optics express, 16(12), pp. 8670-8677.
Unitaid Malaria Diagnostic Technology and Market Landscape, 2nd Edition (2014).
Vink, J.P et al., "An automatic vision-based malaria diagnosis system", Journal of Microscopy 250.3 (2013):166-178.
A European Search Report dated Dec. 14, 2016 which issued during the prosecution of Applicant's European App No. 14800352.8.
A European Search Report dated Mar. 23, 2017. which issued during the prosecution of Applicant's European App No. 14839661.7.
An International Preliminary Report on Patentability dated Feb. 28, 2017, which issued during the prosecution of Applicant's PCT/IL2015/050864.

An International Search Report and a Written Opinion both dated Apr. 18, 2013, for International Application No. PCT/IL2012/050556.
An International Search Report and a Written Opinion both dated Feb. 12, 2015, for International Application No. PCT/IL2014/050770.
An International Search Report and a Written Opinion both dated Jan. 15, 2016, for International Application No. PCT/IL2015/050864.
An International Search Report and a Written Opinion both dated Jan. 23, 2017. which issued during the prosecution of Applicant's PCT/IL2016/051025.
An International Search Report and a Written Opinion both dated Oct. 30, 2014, for International Application No. PCT/IL2014/050585.
An International Search Report and Written Opinion in International Application No. PCT/IB2018/058861, dated Apr. 8, 2019.
An Office Action dated Apr. 2, 2015, which issued during the prosecution of U.S. Appl. No. 13/338,291.
An Office Action dated Apr. 4, 2019 which issued during the prosecution of U.S. Appl. No. 14/914,329.
An Office Action dated Aug. 4, 2017. which issued during the prosecution of U.S. Appl. No. 14/369,251.
An Office Action dated Dec. 24, 2018 which issued during the prosecution of Indian Patent Application No. 3592/2012.
An Office Action dated Feb. 22, 2018 which issued during the prosecution of U.S. Appl. No. 14/369,251.
An Office Action dated Jan. 10, 2018. which issued during the prosecution of U.S. Appl. No. 15/083,610.
An Office Action dated Jan. 28, 2019 which issued during the prosecution of U.S. Appl. No. 15/174,490.
An Office Action dated Jan. 31, 2019 which issued during the prosecution of Indian Patent Application No. 5069/DELNP/2012.
An Office Action dated Jul. 11, 2017. which issued during the prosecution of U.S. Appl. No. 15/174,490.
An Office Action dated Jun. 13, 2017. which issued during the prosecution of U.S. Appl. No. 14/285,672.
An Office Action dated Jun. 4, 2019, which issued during the prosecution of U.S. Appl. No. 14/369,251.
An Office Action dated Jun. 5, 2019, which issued during the prosecution of U.S. Appl. No. 15/174,490.
An Office Action dated Mar. 2, 2017. which issued during the prosecution of U.S. Appl. No. 14/369,251.
An Office Action dated Mar. 23, 2018 which issued during the prosecution of Indian Patent Application No. 4263/DELNP/2014.
An Office Action dated Mar. 26, 2018, which issued during the prosecution of U.S. Appl. No. 14/285,672.
An Office Action dated Nov. 16, 2018 which issued during the prosecution of U.S. Appl. No. 14/914,329.
An Office Action dated Oct. 29, 2014, which issued during the prosecution of U.S. Appl. No. 13/338,291.
An Office Action dated Oct. 5, 2016, which issued during the prosecution of U.S. Appl. No. 14/285,672.
An Office Action dated Sep. 25, 2015, which issued during the prosecution of U.S. Appl. No. 13/338,291.
An Office Action in Indian Application 3592/MUMNO/2015 dated Dec. 24, 2018. 4 pages.
An Office Action dated Dec. 18, 2019, which issued during the prosecution of U.S. Appl. No. 15/174,490.
Notice of Allowance dated Dec. 30, 2015 U.S. Appl. No. 14/440,864.
Notice of Allowance dated Jan. 11, 2016, which issued during the prosecution of U.S. Appl. No. 14/440,864.
Notice of Allowance dated Jan. 19, 2016, which issued during the prosecution of U.S. Appl. No. 13/338,291.
Notice of Allowance dated Mar. 10, 2016, which issued during the prosecution of U.S. Appl. No. 13/338,291.
Notice of Allowance dated Mar. 20, 2019 in U.S. Appl. No. 15/506,997.
Notice of Allowance dated Jul. 10, 2019, which issued during the prosecution of U.S. Appl. No. 15/506,997.
U.S. Appl. No. 61/427,809, filed Dec. 29, 2010.
U.S. Appl. No. 61/870,106, filed Aug. 26, 2013.
U.S. Appl. No. 62/042,388, filed Aug. 27, 2014.

(56) References Cited

OTHER PUBLICATIONS

A Preliminary Examination Report dated Sep. 2019, for Brazilian Application No. BR 11 2014 016072 4.
An Office Action dated Dec. 27, 2021 which issued during the prosecution of U.S. Appl. No. 16/106,085.

* cited by examiner

METHODS AND SYSTEMS FOR DETECTING ENTITIES IN A BIOLOGICAL SAMPLE

CROSS-REFERENCE TO RELATED APPLICATIONS

This application is a continuation of U.S. patent application Ser. No. 14/369,251 to Pollak (published as US 2015/0037806), which is a US national phase application of PCT Application No. PCT/1112012/050556 to Pollak (published as WO 13/098821), filed Dec. 27, 2012, which claims the benefit of:

PCT Application No. PCT/2011/000973 to Bachelet (published as WO 12/090198), filed Dec. 29, 2011; and U.S. Provisional Application No. 61/664,769 to Pollak, filed Jun. 27, 2012.

TECHNOLOGICAL FIELD

The present disclosure concerns diagnostic methods and in particular, methods and systems for detecting pathogens in bodily fluids.

PRIOR ART

References considered to be relevant as background to the presently disclosed subject matter are listed below:

J. Keiser, J. Utzinger, I. Premji Y. Yamagata and B. H. Singer in Annals of Tropical Medicine & Parasitology, Vol. 96, No. 7, 643-654 (2002)

U.S. Pat. No. 5,470,751

On line publication of Centers for Disease Control and Prevention CDC, Diagnostic Procedures, 2009 "Blood specimens: Microscopic Examination" at http://www.dpd.cdc.gov/dpdx/HTML/Frames/DiagnosticProcedures/body_dp_bloodexamin.htm Acknowledgement of the above references herein is not to be inferred as meaning that these are in any way relevant to the patentability of the presently disclosed subject matter.

BACKGROUND

Staining is a technique frequently used in biology and medicine to highlight structures in biological tissues for viewing, often with the aid of different microscopes. Stains may be used to define and examine bulk tissues (highlighting, for example, muscle fibers or connective tissue), cell populations (classifying different blood cells, for instance), or organelles within individual cells.

Cell staining is used to better visualize cells and cell components under a microscope. By using different stains, one can preferentially stain certain cell components, such as a nucleus or a cell wall, or the entire cell. The stains can be used on fixed, or non-living cells, as well as on living cells.

Cell staining techniques are also often used to detect a pathogen in a blood sample. One important pathogen is the malaria.

The first dye synthesized for detection by staining methylene blue, in 1876. Six years later, it was used to discover tuberde bacillus. Within the years, modifications of MB were employed, including, "ripened" MB in combination with other dyes, such as eosin, which allowed differentiation between blood cells and the nuclei of malarial parasites, as well as the combination of MB methylene blue demethylation with glycerol as a stabilizing agent in methanol solvent, known as the Malachowski-Wright-Giemsa stain.

J. Keiser et al. describe Acridine Orange in comparison to Giemsa stain, for malaria diagnosis, including its diagnostic performance, its promotion and implementation and the implications for malaria control.

U.S. Pat. No. 5,470,751 describes another reagent for staining malaria infected cells and a method for detecting malaria infected cells using the same, wherein the reagent is a staining solution comprising at least one first dye of an Auramine analogue, such as Auramine O and at least one second dye of a condensed benzene derivative, such as 3,3'-diethyl-2,2'-oxacarbocyanine iodide. A test sample is treated with reagent to stain malaria infected cells. The stained malaria infected cells are then optically detected.

In addition, the Centers for Disease Control and Prevention CDC, Diagnostic Procedures, 2009 describes under the heading "*Blood specimens: Microscopic Examination*" the Kawamoto technique for the detection of blood parasites, such as malaria parasites, using fluorescent dyes that stain nucleic acids. As discussed in this publication, in the Kawamoto technique, blood smears on a slide are stained with acridine orange (AO) and examined with either a fluorescence microscope or a light microscope adapted with an interference filter system. This results in a differential staining of nuclear DNA in green and of cytoplasmic RNA in red, which allows recognition of the parasites.

GENERAL DESCRIPTION

The present disclosure provides, in accordance with a first of its aspects, a method of detecting a pathogen infection in a sample, the method comprising:

staining said bodily sample with two or more dyes, comprising at least one dye predominantly staining DNA to thereby provide differential staining between DNA and at least one other cellular component being different from DNA;

identifying at least a first stained area comprising the DNA, if exists in the sample, and at least one other stained area comprising the other cellular component;

extracting structural features for the first stained area and the at least one other stained area, said structural features comprise at least one of (i) size of at least one of the first stained area and one other stained area and (ii) location of said first stained area and said at least one other stained area one with respect to the other; and determining the presence of a suspected pathogen in the sample if a first stained area was identified and said structural features conform to structural features predetermined as characterizing the suspected pathogen.

In accordance with a second aspect, the present disclosure provides a kit comprising:

a first dye predominantly staining DNA;

a second dye for staining at least one other cellular component being different from DNA;

instructions for use of said first dye and said second dye in determining presence of a suspected pathogen in a sample, In accordance with a third aspect, the present disclosure provides a system comprising:

an image capturing component configured and operable to acquire at least one optical image of a stained area in a sample, the stained area comprising a first stained area corresponding predominantly to DNA and at least one other stained area corresponding to at least one other cellular component being different from DNA;

an image processing unit configured to i) extract structural features of said at least first stained area and said one other stained area, said structural features comprise at least one of (i) size of at least one of said first stained area, and (ii) one other stained area; and a location of said first stained area and said one other stained area one with respect to the other; and ii) determine the presence of a suspected pathogen in the bodily sample, if a first stained area is identified and said structural features conform to structural features predetermined as characterizing a pathogen infection, Yet, in accordance with a fourth aspect, the present disclosure provides a processing unit for identifying a pathogen in a sample, comprising:

input module configured and operable to receive data corresponding to a stained object in the sample comprising at least a first stained area corresponding predominantly to DNA and at least one other stained area corresponding to at least one other cellular component being different from DNA, and an image processing unit configured and operable to process said data corresponding to said stained object, the processing comprises:

extracting structural features for the at least the first stained area and second stain area in the stained object, said structural features comprise at least one of (i) area of at least one of the first and the one other stained area and (ii) a location of said first stained area and said one other stained area one with respect to the other; and providing a value or combination of values being indicative of the presence or absence of a suspected pathogen in the sample, if said structural features conform to structural features predetermined as characterizing the suspected pathogen In accordance with a fifth aspect, the present disclosure provides a computer program product comprising a computer useable medium having computer readable program code embodied therein for detecting a pathogen infection in a sample being stained with two or more dyes, the computer program product comprising:

computer readable program code for causing the computer to identify in the stained object at least a first stained area corresponding predominantly to DNA and at least one other stained area corresponding to at least one other cellular component being different from DNA;

computer readable program code for causing the computer to extract structural features for the at least a first stained area and one other stain area, said structural features comprise at least one of (i) area of at least one of the first and one other stained areas and (ii) location of said first stained area and said one other stained area one with respect to the other;

computer readable program code for causing the computer to determine a value or combination of values being indicative of the presence of a suspected pathogen in the sample if said structural features conform to structural features predetermined as characterizing the suspected pathogen infection.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
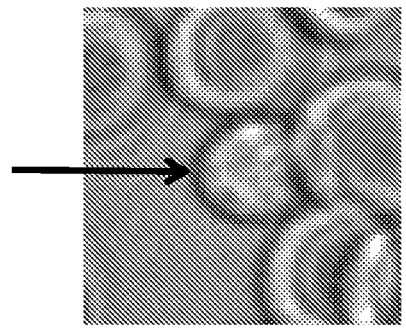
FIGS. 1A-1F show images obtained at three different exposures; the bright field (FIGS. 1A, 1D), blue fluorescence (365 nm, FIGS. 1B and 1E) and UV fluorescence (475 nm, FIGS. 1C, 1F) images of white blood cells (FIGS. 1A-1C) and malaria infected red blood cells (FIGS. 1D-1F).

The present invention is based on the development of methods for differential stain different components in a blood sample to thereby allow an almost instant detection of an infection in the blood.

Specifically, it has been found by the inventors that staining of a blood sample with acridine orange (AO) reagent allows differentiation between DNA containing pathogens and, for example, platelets, reticulocytes, Howell-Jolly bodies, and bacteria such as *Staphylococcus epidermidis*.

It has been further found that staining of a blood sample with AO and Hoechst reagents and by employing an image analysis of the stained object including the two different stained areas (the object being an image in the field of view comprising the stained areas under examination), allowed detection of malaria infection in the blood sample. In this connection, the inventors have found that in addition to detecting two different stained areas in the viewed stained object (of the sample), it is sometimes also important to take into consideration some spatial features of the stained areas, such as the size or dimensions of each stained area and/or the spatial relationship therebetween.

The inventors have also determined that in order to detect a pathogen in the blood sample, at least one dye should stain deoxyribonucleic nucleic acid (DNA) with preference over staining of other cellular components.

It has been further found by the inventors that the diagnostic sensitivity obtained by using two dyes, one predominantly staining DNA, is above 95%, and even above 97% or 99%.

Further, it has been found, and was also shown in the following example, that the method disclosed herein allows identifying the presence of a pathogen at low counts/O. For example, the example provided herein shows that a parasite, such as *Plasmodium* may be detected in the blood even at a count below 1,000 parasites per μl and even at a low count of about 20 parasites per μl.

Thus, in accordance with a first aspect, the present disclosure provides a method of detecting a pathogen infection in a sample, the method comprising:

staining said bodily sample with two or more dyes, with at least one dye predominantly staining DNA to thereby provide differential staining between DNA and at least one other cellular component, being different from DNA;

identifying at least a first stained area comprising the DNA, if exists in the sample and at least one other stained area comprising the other cellular component;

extracting spatial features for the first stained area and the at least one other stained area, said spatial features comprise at least one of: (i) size of at least one of the first stained area and one other stained area; and (ii) location of the first stained area and the at least one other stained area one with respect to the other;

determining the presence of a pathogen in the sample if a first stained area was identified and said spatial features conform to (namely, matches, corresponds to, falls within, is associated with), a value or a combination of values predetermined as characterizing a suspected pathogen infection.

As appreciated, while the invention is described in the following detailed description with reference to a method of detecting a pathogen infection in a sample, such as a blood sample, it is to be understood that the present disclosure also encompass a kit for performing the invention, a system, a processing unit and other aspects, as disclosed herein, The method of the invention is applicable for a variety of samples. In some embodiments, the sample is a bodily sample. In some embodiments, the bodily sample is a fluid bodily sample such as, without being limited thereto, blood, saliva, semen, sweat, sputum, vaginal fluid, stool, breast milk, bronchoalveolar lavage, gastric lavage, tears and nasal discharge.

In some embodiments, the bodily sample is a blood sample.

In some embodiments, the blood sample is selected from whole blood sample, red blood cell sample, buffy coat sample, plasma sample, serum sample, a sample from any other blood fraction, or any combination thereof.

The bodily sample may be from any living creature but preferably from warm blooded animals.

In some embodiments, the bodily sample is a sample from a mammal.

In some embodiments, the bodily sample is one taken from a human body.

In some other embodiments, the sample is taken from any domestic animal, zoo animals and farm animals, including but not limited to dogs, cats, horses, cows and sheep.

In some embodiments, the bodily sample may be taken from animals that act as disease vectors including deer or rats.

In some other embodiments, the sample is an environmental sample, such as, without being limited thereto water (e.g. groundwater) sample, surface swab, soil sample, air sample, or any combination thereof.

In some embodiments, the sample is a food sample, such as, without being limited thereto, meat sample, dairy sample, water sample, wash-liquid sample, beverage sample, and any combination thereof.

As a first stage in the method disclosed herein, the sample is stained with at least two dyes providing, under suitable conditions, two distinct stained areas in the sample.

A stained area may be defined, inter alia, with respect to, for example, background or collateral staining. For example, an intensity-based threshold, contrast-based threshold, edge detection, background subtraction, normalization, or combination thereof may be applied to define the stained area. Additionally, the definition of stained area may allow, inter alia, for diffuse boundaries, for example, by using a brightness-weighted sum/integral.

In some embodiments, such as in the case of membrane staining, a first stained area residing within a second stained area may be defined to include a case wherein the first area resides within the area circumscribed within the second area. For example, membrane staining of red blood cells may result in a second stained area that resembles narrow lines around the circumference of the cell (as viewed in a two-dimensional microscope image) in such a case, it may be determined that the first area resides within said second area if it falls within the stained cell circumference.

In some embodiments, standard microscopic sample preparation may be required for staining the sample. For example, sample preparation may take advantage of the well-known thin smear or thick smear method for blood smear preparation. As an alternative example, a drop of the sample is placed in the middle of a clean slide together with, before or after placing the dye and a cover slip is gently placed over the drop at an angle, with one edge touching the slide first. The liquid is then allowed to spread out between the two pieces of glass without applying pressure.

When referring to a dye it is to be understood as encompassing any chemical or biological substance that is capable of staining a component of a biological cell, to enhance contract and highlight structures of the stained object, be it a cell or part of a cell. The dye may have a class preference or specificity, e.g. may have preference or specificity to staining of nucleic acids and among the nucleic acid, to DNA or RNA, preference or specificity to amino acids, to lipids, carbohydrates etc.

When referring to preference or predominant staining it is to be understood that the dye stains one other cellular component in a particular color or fluorescence that is at least twice, three times, four times or even 10 times greater in its intensity than its staining intensity to another cellular component at that same color or fluorescence spectrum.

In some embodiments, when referring to preference or predominant staining it is to be understood that the dye has affinity (molecular attraction) to one cellular component (in the particular color or fluorescence spectrum) that is at least twice, three times, four times or even 10 times greater in its affinity to another cellular component (at that same color or fluorescence spectrum).

In some further embodiments, when referring to preference or predominant staining it is to be understood that the staining of DNA by the dye is stable or has more stability as compared to its staining of other components. Stability may be understood to mean that the staining produced by the dye remains substantially consistent for at least 30 minutes after being brought into contact with the dye, at times, at least 1 hour, 2 hours or even 5 hours after staining the sample with the dye having preference to DNA. Alternatively, stability may be understood to mean that the staining produced by the dye remains substantially consistent during exposure to light (e.g. light used for fluorescence excitation) for at least 0.25 seconds, 1 second, or even 15 seconds of exposure.

In this context, it is to be understood that the dye having preference to DNA may also stain other cellular components but with lower attraction or lower intensity or with a different florescence response (excitation spectrum anchor emission spectrum) such that it allows the greater enhancement of the DNA, which the dye has preference. For example, as will be further discussed below, under some conditions a dye may predominantly stain DNA, however, under some other conditions, the same dye may stain RNA.

Similarly, the staining of one other cellular component should be understood as encompassing staining of one or more cellular components other than DNA. This may also include staining of one or more cellular components in addition to DNA, but with no preference or lower preference to staining of DNA.

In some embodiments, the dyes are not cell type specific. In other words, the dye is not specific to a particular pathogen or to a particular stage of the life cycle of a particular pathogen or to a particular cell of the host being infected therewith and will stain a cell component irrespective of its origin, e.g. a DNA sequence or structure per se, an RNA sequence or structure per se, protein per se, etc.

The existence of a first stained area is determined based on various factors that may relate, inter alia, to the intensity of the stain, the shape of the stain, the variability or consistency of the stain etc. Once a first stained area is determined to exist, it is ascribed to the presence of DNA.

The method also provides a stained area of at least one other cell component being different from DNA. The stained area may be obtained from the same dye, under different conditions or by the use of a different dye.

Without being limited thereto, the at least one other cellular component is selected from the group consisting of RNA, proteins, lipids, membrane, cytoplasm, ribosomes, carbohydrates, glucans, glycoproteins, endoplasmatic reticuli, or any combination thereof.

In some embodiments, the at least one other cellular component is RNA.

There are a variety of dyes that may be used in accordance with the present disclosure. In some embodiments, the dye is a chromophore or fluorophore.

Dyes such as the Giemsa stain are known as chromogenic—their effect is to provide color or opacity to the sample and are visible, for example, in bright field microscopy.

In some embodiments, the dye provides fluorescent staining of the sample. Fluorescence is visualized by illuminating the sample with an "excitation" spectrum of light, which results in an "emission" at a distinct spectrum of light. Amongst the potential advantages of fluorescent stains is that the regions of the sample that are not stained show up as dark or nearly dark, thereby typically providing greater contrast between stained and unstained areas than chromogenic stains. Acridine Orange (AO) is an example of a dye used to fluorescent staining of biological samples.

In some embodiments, the dye is a cell permeating dye.

Without being limited thereto, a dye that predominantly stains DNA may be any member of the group consisting of acridine orange (AO, N,N,N',N'-Tetramethylacridine-3,6-diamine, green staining), Hoechst family, DAPI (4',6-diamidino-2-phenylindole), ethidium bromide (3,8-Diamino-5-ethyl-6-phenylphenanthridinium bromide), propidium iodide (2,7-Diamino-9-phenyl-10 (diethylaminopropyl)-phenanthridium iodide methiodide), SYBR family, YOYO, DRAQ family, SYTO family, TOTO family, or any combination thereof. Additionally the dye comprises a chemical modification of any of the aforementioned dyes that preserves its DNA preference.

Without being limited thereto, a dye that does not predominantly stain DNA may be any member of the group consisting of crystal violet (Tris(4-(dimethylamino)phenyl) methylium chloride), Hematoxylin stains, eosin stains, Safranin (azonium compounds of symmetrical 2,8-dimethyl-3,7-diamino-phenazine), acridine orange (AO, N,N, N',N'-Tetramethylacridine-3,6-diamine, red staining), acid-Schiff stains, Masson's stain, Prussian blue, or any component or combination thereof. Many more stains that do not predominantly stain DNA are known in the art.

Dyes such as AO provide different fluorescence spectra for different cellular components. When AO stains DNA at neutral pH, it has an excitation maximum at 502 nm (cyan) and an emission maximum at 525 nm (green); when it stains RNA at neutral pH, the excitation maximum shifts to 460 nm (blue) and the emission maximum shifts to 650 nm (red). As such, it allows differential staining between DNA and RNA, depending on the excitation wavelength and conditions of the sample.

The Hoechst family of dyes are known by the chemical formula $C_{25}H_{26}N_6R$, with R representing a variety of possible substituents, such as, without being limited thereto, —OH (Hoechst 33258); —$CH_2CH_3$ (Hoechst 33342), —$N(CH_3)_2$ (Hoechst 34580), —$SO_2NH_2$ (Hoechst S769121).

In some embodiments, the method involves the combined staining with at least two dyes, the first dye being a member of the Hoechst family and the second dye being acridine orange.

When referring to a combination of two or more stains, it is to be appreciated that the two or more dyes may be added to the sample simultaneously or in sequence. Similarly, the respective stained areas may be obtained simultaneously or in sequence, as long as there is a time point that allows viewing two or more differently stained areas in the same sample.

In one embodiment, the method employs a combination of AO with the membrane-permeable dye that is essentially specific to nuclear DNA (e.g. Hoechst 33342, yielding a blue emission).

According to this embodiment, AO allows using the red-emission or a combination of the green and red emissions to stain the pathogen's cytoplasm (and possibly also the nucleus, but without substantially interfering with the Hoechst staining).

In some embodiments, the combination of AO and Hoechst allows the detection of a parasite. According to this embodiment and without being limited thereto, for the detection of a parasite, such as a member of the *Plasmodium* species, the concentration of Hoechst reagent such as Hoechst 33342 may be 10 μg/mL, but other possible values may be used as well, for example in the range between 3 μg/mL and 250 μg/mL; and AO may be used at 1.5 μg/mL, but other possible values may be used as well, for example in the range between 0.2 μg/mL and 125 μg/mL.

In some embodiments, the amount of AO and Hoechst reagent to be used is determined so as to provide, in the biological sample, a ratio therebetween. Accordingly, the Hoechst:AO ratio may be in the range of between 50:1 to 1:1, at times, about 7.5:1.

A same or similar ratio may also be applicable for other dye combinations, a first dye staining predominantly DNA and the other dye, one other component, as defined, namely, a ratio between the first dye and other dye in the range of between 50:1 to 1:1.

AO may additionally or alternatively be used to stain, for example, *Plasmodium* cytoplasm and/or food vacuole, but not the cytoplasm of the red blood cell (RBC) that the parasite may be inside, allowing the parasite's body to be seen without being obscured by an RBC even if present within the RBC.

Appropriate concentrations may be optimized with respect to factors such as the particular dye combination, desired duration of stain incubation, brightness of resulting color or fluorescence, and character of the resulting staining.

In some embodiments, the method disclosed herein is applicable for the detection of an infection by a DNA-carrying pathogen. As such, at least the first dye stains at least the DNA, if present in the sample to thereby provide a first stained area indicative of the presence of the DNA carrying pathogen in the sample.

The pathogen may be any infectious microorganism. An some embodiments, the pathogen is a eukaryotic parasite. When referring to eukaryotic parasite, in the context of the present disclosure, it is to be understood as encompassing one cell parasites and multicellular parasites but also fungi, such as yeast (e.g. *Candida*) and *Aspergillus*.

In some embodiments, the pathogens are bacteria. This includes, for example and without being limited thereto, *Escherichia coil, Staphylococcus aureus, Microbacterium tuberculosis, Salmonella* species, *Borrelia* species and *Treponema pallidum* and others known.

In some embodiments, the pathogen is a eukaryotic parasite. In accordance with this embodiment, the parasite may be a one cell parasite, such as protozoa. This includes genital protozoa, e.g. *Trichomonas vaginalis*, nervous system protozoa, e.g. *Naegleria fowleri* fecal protozoa, e.g. *Giardia lamblia*, blood protozoa. In some embodiments, the pathogen may be a multicellular parasite, such as *Wuchereria bancroft*, *Brugia malayi*, *Brugia timori*, *Mansonella streptocerca*, or *Onchocerca volvulus*.

In some embodiments, the parasite is a blood protozoa selected from the genuses consisting of *Trypanosoma* (causing Chagas disease and African sleeping sickness), *Plasmodium* (causing Malaria); Toxoplasma (causing Toxoplasmosis); *Babesia* (causing Babesiosis).

Specifically, when referring to *Plasmodium* it is to be understood as encompassing at least any member of the group consisting of *Plasmodium falciparum* (*P. falciparum*), *Plasmodium vivax* (*P. vivax*), *Plasmodium ovale* (*P. ovale*), *Plasmodium malariae* (*P. malariae*), and *Plasmodium knowlesi* (*P. knowlesi*).

In some embodiments, pathogen is understood to mean a particular stage of the life cycle of a particular pathogen or group thereof. For example, the invention disclosed herein can be applied specifically to the detection of trophozoites, schizonts or gametocytes of *Plasmodium* species or *P. falciparum* in particular.

As may be appreciated, the method disclosed herein may be applicable for the detection of multiple pathogens using the same conditions and/or in the same sample, e.g. same combination of dyes, same test conditions etc., as well as for the detection of a pathogen at multiple stages of its life cycle. In some embodiments, the method disclosed herein may determine which one or more of the multiple pathogens (or life stages) is suspected.

In some embodiments, the method disclosed herein is for detecting *Plasmodium* infection in a human blood sample, the method comprising:
  staining the human blood sample with at least two dyes, under conditions that allow at least staining of DNA and at least one other cellular component being different from DNA;
  identifying at least a first stained area comprising the DNA, if exists in the blood sample, and at least one other stained area comprising one other cellular component in the blood sample;
  extracting structural features for the first stained area and the at least one other stained area, said spatial features comprising size of at least one of the first stained area and one other stained area and a location of the first stained area and the at least one other stained area one with respect to the other;
  determining value or combination of values being indicative of the presence of suspected *Plasmodium* in the blood if a first stained area was identified and said structural features fall within limitations predetermined as characterizing a pathogen infection.

In some embodiments relating to determination of the presence of *Plasmodium* in the blood, the stained object is obtained by staining the blood sample with a combination of acridine orange (AO) and Hoechst dye, in particular, Hoechst 33342 with a concentration ratio between AO and Hoechst 33342 in the range of 1:50 and 1:1, at times, even in the range of 1:7.5.

In accordance with the above embodiment, the method is applicable for detection of malaria infection in a human blood sample.

Once the sample is stained with the one or more dyes, at least one stained object is obtained and the method then involves selecting at least one stained object in the sample and obtaining structural or spatial features of the stained object.

When referring to spatial or structural features of a stained object it is to be understood as encompassing any measurable feature of the stained areas in the selected stained object. The features may be presented as a discrete value or as a range of values characterizing the stained area.

In some embodiments, the structural features include at least one of the size (e.g. dimension, length, circumference, minimum width, maximum width, or area) of the stained areas and/or the location of the first stained area with respect to the location of the other stained area or areas. In other words, the method may be performed based at least one either determining dimensions, e.g. area of the stained areas, or on the location of the first stained area with respect to the location of the other stained area or areas. These features may be combined also with one or more additional features.

The additional structural features may include, without being limited thereto, shape of stained area(s), pattern of movement of stained area(s), intensity of stained area(s), color of stained area, texture (contour) of stained area, sharpness of boundary of stained area, pattern of staining in intensity or color, overlap of stained area with other stained areas or image features, relative size of stained area to other stained areas or image features, proximity or contact of stained are to other stained areas or image features.

In some embodiments, the bodily sample is a blood sample.

In some embodiments, the pathogen is a blood parasite.

In some embodiments, the bodily sample is human blood and the pathogen is *Plasmodium* species responsible for human malaria, such as those selected from the group consisting of *P. falciparum*, *P. vivax*, *P. ovale* and *P. malariae*.

When the bodily sample is a blood sample, the extraction of structural features comprises selecting a stained object in the blood sample that comprises the first stained area and the at least one other stained area.

Based on the stained areas and the analysis of the structural features a high probability of the sample being infected with a suspected pathogen is determined. Thus, in the context of the present disclosure, when referring to determination of presence of a pathogen or suspected pathogen it is to be understood that any one of the following is determined:
  that one or more suspected pathogen are present in the sample;
  that one or more suspected pathogens are present in the sample at a confidence levels above a predefined threshold; the confidence levels may increase or a final determination of the presence of a suspected pathogen may require one or more additional analysis steps.
  that one or more suspected pathogens may be present in the sample with a determined or estimated confidence scores or probabilities that are available for additional analysis steps In accordance with some embodiments, a suspected pathogen is determined to be present in the sample if a first stained area is identified (being indicative of the presence of DNA in the sample), and the first stained area abuts with, is in close proximity to, or resides within the one other stained area and the size of at least one of the first stain, i.e. the DNA containing area, and of the one other stain is within a predetermined range. For example, a DNA containing area often lies near an area stained for RNA, which exists in the cytoplasm.

In accordance with some other embodiments the suspected pathogen is determined to be present in the sample if a first stained area is identified (again, being indicative of the presence of DNA in the sample) and the size of the first stained area satisfies a predetermined relation with respect to the size of the one stained area. This criterion can be used, for example, to differentiate targeted eukaryotic parasites from bacteria: in eukaryotic cells, the area predominantly stained for DNA should be smaller than a cytoplasmic staining, indicating a distinct nucleus that is not present in bacteria.

In accordance with yet some embodiments, the presence of a suspected pathogen is determined if a first stained area is identified and the dimensions or area of the first stained area is within a range of values predetermined to be associated with the particular pathogen or with a particular stage of the life cycle of a particular pathogen. For example, if the pathogen is one causing malaria (i.e. *Plasmodium*), the area of the first stained area would typically not be below 0.2 $\mu m^2$ or above 20 $\mu m^2$ or would be in the range of 0.2 $\mu m^2$ to 20 $\mu m^2$. In some embodiments, the area of the first stained area in detection of *Plasmodium* would not be below 0.8 $\mu m^2$ or above 13 $\mu m^2$ or would be within the range of 0.8 $\mu m^2$ to 1.3 $\mu m^2$.

In accordance with some other embodiments the presence of a suspected pathogen is determined to be in the sample if a first stained area is identified and the areas of the one other stained area are within a range of values predetermined to be associated with the particular pathogen or a particular stage of the life cycle of a particular pathogen. For example, if the pathogen is one causing malaria (i.e. *Plasmodium*), the area, for example, a cytoplasm, of the other stained area would typically not be below 0.8 $\mu m^2$ or above 65 $\mu m^2$ or would be in the range of 0.8 $\mu m^2$ to 65 $\mu m^2$. In some embodiments for detecting malaria infection, the area of the other stained area is not below 1.6 $\mu m^2$ or does not exceed 40 $\mu m^2$ or is in the range of 1.6 $\mu m^2$ to 40 $\mu m^2$.

Considering the above features, it is understood that in accordance with some embodiments of the present disclosure, particular area of the first stained area cannot exceed particular area of the one other stained area. Similarly, the dimensions of the first stained area should be statistically significant (e.g. by t-test) smaller than the dimensions of the other stained area.

In some other embodiments, the presence of a suspected pathogen is determined to be in the sample if a first stained area is identified and the first stained area occupies a predetermined % volume of the all other stained areas. For example, when referring to malaria, the first stained area would typically occupy between 12% to 60% of said one other stained area.

In accordance with some other embodiments the presence of a suspected pathogen is determined to be in the sample if a first stained area is identified and the first stained area and the one other stained area have predetermined shapes. For example, the trypomastigote stage of *Trypanosoma brucei* is known to have an elongated, rod like shape. Other shapes may include, without being limited thereto, spiral, oval, elongated and spherical properties.

In accordance with some embodiments, the presence of a suspected pathogen is determined to be in the sample if a first stained area is identified and the first stained area has a variability in intensities that is above a predetermined threshold. The variability of intensities may appear as a cluster of more than one area stained with the first stain (plurality of first stained area) or as an irregular shaped first stained area having different shades of color or fluorescence. This may reflect, for example, a multinucleate stage in the development of a protozoan, such as schizonts of *Plasmodium*.

Yet further, in accordance with some embodiments the presence of a suspected pathogen is determined if a first stained area is identified and the pattern of movement directionality and/or velocity) of the stained object corresponds with a pattern predetermined to be associates with the suspected pathogen. For example, when considering *Trypanosoma brucei*, its motion (motility) is expected to occur at a characteristic pattern. As such, when the sample is stained with AO and Hoechst staining, the movement of the AO stained area may be analyzed to confirm a match or an expected correlation with the expected pattern.

In yet some other embodiments, the presence of a suspected pathogen is determined if during movement of the stained object the first stained area is maintained within boundaries of the one other stained area. Thus, when referring to the above example with *Trypanosoma brucei*, the movement of the Hoechst stained area may be analyzed to ensure that a putative nucleus remains at all times within the moving AO stained area.

The structural features may be determined by simple viewing the sample, however, in some embodiments they are preferably determined based on one or more optical images of the sample. Thus, in accordance with some embodiments, the method comprises capturing at least one optical image of the stained object and extracting the structural features from the at least one optical image.

At times, particularly when the structural parameter includes motion or movement of the stained object, more than one optical image is captured and the structural parameter of motion is determined based on a sequence of images in time.

Needless that state, the more accumulated (or collected) information of structural parameter(s) of the stained object, the more accurate the determination and identification of a pathogen in the sample may be.

The structural features may be analyzed manually, or by the use of a dedicated system for allowing an automated and as such, relatively fast detection and/or identification of the pathogen in the bodily sample. The result of the analysis may retrieve a Yes/No indication of the presence of a pathogen, a probabilistic indication of the presence of a pathogen, images of a suspected pathogen for further analysis (manual or automatic) and/or may provide a more specific result, including the type of the pathogen, level of invention (count/μl) etc.

The use of an automated system may be of significance, not only for overcoming human errors in analyzing the stained objects in the sample and saving time and labor, but also since certain components of a bodily sample may not stain immediately and/or the degree of staining may vary significantly over time, as is the case in sometimes with Hoechst 33342 staining of blood contaminated cells. Consequently, image characteristics may vary depending on how quickly the sample is analyzed. As such, there is an advantage of having an automated system allowing the rapid, or even almost instantaneous, imaging and analysis of the stained sample.

Thus, in accordance with a further aspect of the present disclosure there is provided a system comprising:
an image capturing component configured and operable to capture at least one optical image of a stained area in a sample, the stained area comprising a first stained area corresponding predominantly to DNA and at least one other stained area corresponding to at least one other cellular component being different from DNA;

an image processing unit configured to extract structural features of said at least first stained area and said one other stained area, said structural features comprising at least size of at least one of said first stained area, and one other stained area; and a location of the first stained area and said one other stained area one with respect to the other; and determine that a pathogen is present in the sample, if a first stained area is identified and the structural features conform to structural features predetermined as characterizing a pathogen infection.

In some embodiments, the system also includes an output unit for providing an output comprising a value or combination of values being indicative of the presence or absence of suspected pathogens in the sample.

In some embodiments, the system is preferably computer-based using a collection of parameters being stored therein and corresponding to, inter alia, structural features associated with at least one defined pathogen: The parameters may, for example, include expected values or ranges of values of the structural features, associated with a pathogen, or parameters that control the execution of machine-learning or data analysis algorithms. The parameters may be derived from information gathered a priori or simultaneously obtained based on reference samples including pre-determined pathogens.

The parameters may also comprise information relating to the behavior of a pathogen, or cell infected with a pathogen, such as motility and variations in features depending on the particular stage of the life cycle of a particular pathogen.

The parameters may also comprise information regarding conditions to be used for the detection of a pathogen on a type of bodily sample, e.g. on blood sample, statistical information regarding the staining qualities and variability of a set of dyes to be used for a particular bodily fluid, alternative dye combinations or condition combinations, etc.

In some embodiments, the collection of stored parameters comprises parameters associated with a plurality of pathogens. In some embodiments, the collection of stored parameters comprises parameters that associated with determining which one or more pathogens is suspected.

In some embodiments, the collection of parameters is associated with blood borne pathogens. In some other embodiments, the collection of parameters is associated with blood parasites. In some particular embodiments, the collection of parameters is associated with pathogens that harbor the human blood, in particular, of a *Plasmodium* species responsible for human malaria, such as those selected from the group consisting of *P. falciparum, P. vivax, P. ovate* and *P. malariae*.

Further provided by the present disclosure is an image processing unit for identifying a pathogen in a sample, comprising:

input module configured and operable to receive (image) data corresponding to the stained object in the sample comprising at least a first stained area corresponding predominantly to DNA and at least one other stained area corresponding to at least one other cellular component different from DNA, and an image processing unit configured and operable to process the data corresponding to the stained object, the processing comprises:

extracting structural features for the at least the first stained area and the one other stained area in the stained object, said structural features comprising at least one of (i) size of at least one of the first and the one other stained areas and (ii) location of said first stained area and said one other stained area one with respect to the other; and providing a value or combination of values being indicative of the presence or absence of a pathogen in the sample, if said structural features conform to structural features predetermined as characterizing a suspected pathogen.

Several modes of operation may be used with respect to the system and image processing unit, Automated as well as manual and semi-automated systems can be employed.

With respect to the system, the image capturing component may be any device configured and operable to acquire at least one optical image of the stained object being selected, for example, a CCD or CMOS camera. The image capturing component may be equipped with conventional functionalities, such as focus functionalities. The image capturing component may also include lenses, aperture and shutter.

The image capturing component provides image data for processing by the image processing unit. The image data in the context of image analysis is based on a collection of pixel information that essentially covers one or more Regions of Interest (ROI).

The image data typically including the pixel information may be presented in any available format, including, without being limited thereto, Tagged Image File Format (TIFF), Joint Photographic Experts Group (JPEG), Graphic Image Format (GIF), Portable Network Graphics (PNG), Portable Document Format (PDF), bitmap (BMP), and raw image-sensor data. Image data can be in a compressed data format or in an uncompressed data format; may relate to any gray or color scale; can include bitmap data, or a portion of a bitmap file containing bitmap data.

Once one or more images are captured, they are processed by the image processing unit. The processing by the processing unit is configured and operable to provide one or more values of structural features of the stained areas. In other words, based on image analysis techniques, various output values relating to structural features of the stained areas are determined, which may allow the identification of the presence or absence of the suspected pathogen in the sample or estimation of the probability of presence therein. The values may include the dimensions of one or more other stained areas in the ROI, the relationship between the stained areas, and/or averages, compounding or statistics of values pertaining to structural features. The processing may include, in some embodiments, analyzing the one or more values or combination of values corresponding to structural features with respect to the parameters e.g. values or ranges of values or appropriate machine-learning weights) that have been a priori determined for characterizing one or more pathogens, or differences therebetween.

The image analysis can be based on one or more of the common practices such as contour detection, image parameter derivatives, shape detection, image reconstruction, segmentation, image differencing, pattern matching, matched filtering, machine learning and geometric hashing.

Data processing by the image processing unit may use a classification module. The classification module can be provided with at least one structural parameter previously determined for a pathogen. The classification module can analyze the structural features provided and deduce a selection of possible pathogens being identified. By way of an illustration, a classifier can identify a plurality of possible pathogens or a single type of pathogen.

In particular embodiments, the structural features determined are associated to an expected pathogen and these are analyzed with respect to the pre-defined parameters.

It should be noted that the identification of a single pathogen may be a complex process which includes different combinations of features. Therefore, structural features determined following the use of a particular combination of dyes can be used as criteria for subsequent analysis of a further combination of dyes. For example, structural features identified in a previous analysis can be used to continue the identification process while focusing of a subset of possible combination of dyes. For example, in a biological family level of identification of a pathogen, the results of previous analysis may provide a list of possible best filter(s) selection to be used in a next round of analysis.

In some embodiments, image analysis and determination of the presence of suspected pathogens or a value or values indicative with the presence of suspected pathogens can take advantage of one or more machine-learning algorithms, which operate on a plurality of structural features or related values. Such algorithms include without limitation Support Vector Machines (SVM), Artificial neural networks, Naive Bayes classifiers, Bayesian networks, Decision trees, Nearest Neighbor Algorithms, Random Forests, Boosting, Regression analysis, Linear classifiers, Quadratic classifiers, k-nearest neighbor, Hidden Markov models and any combination thereof. The result of the one or more machine-learning algorithms can comprise one or more confidence score, probabilities and/or yes/no decisions.

As appreciated, the more features determined in the analysis—the more precise is the identification process. By using a plurality of dyes to induce a plurality of structural features, the risk for misdetection or misclassification is reduced. However, added features may also correspond to increased computational or operational load. Some embodiments strive to balance the added benefit of added features with the associate load drawbacks.

Based on the value or combination of values obtained by the analysis, various decisions are made by the processing unit as to the presence or absence of a pathogen in the sample, including, at times, the type of the pathogen (qualitative identification) and/or the amount (quantitative identification) of the pathogen in the sample.

The processing unit is also configured to communicate with an output unit. Thus, based on the output value or values of the structural features determined by the processing unit, an output signal or output signals indicative of presence or absence of at least one pathogen and in some embodiments, the type of the pathogen, in the acquired image is provided by an output unit.

The output may be provided in any acceptable form, including a graph, graphic or text displayed on a monitor of a control unit, a printout, as a voice message, or a user's smartphone display, for accepting processed data from the processing utility and displaying information relating to the structural features obtained and/or associated values determining the presence and optionally the identity of a pathogenic infection, using, lists, tables, graphs etc. A monitor may be connected to a printer for printing the output.

The processing unit may also include a user interface module, e.g. a keyboard, or a touch screen for allowing a practitioner, performing the method of some embodiments of the invention, to control the operation of the system, including, inter alia, input data with respect to the examined bodily fluid source, date, place, etc.) conditions of operating the system, types of dyes used, number of images to be taken, time interval between images, etc.

At times, image analysis may also involve adjustment or normalization of image brightness on the basis of degree of staining of the sample. These may be based on, for example, identifying one or more of brightest and/or dimmest pixel values in the image or set of image (for example, corresponding to a particular sample), average brightness of brightest and/or dimmest area, and/or image histogram. Such features may be extracted from a representative image (not necessarily the one being normalized) from statistical analysis of multiple images. The features used for normalization may be based on a single or multiple images, which may be captured using different excitation wavelengths (as in AO providing different colors under different illumination wavelengths).

Image brightness may also be adjusted using other control means, such as image capturing component exposure time and/or brightness of illumination.

Further, the conditions of operating the system may allow timing of the image acquisition, e.g. to allow sufficient incubation time with the one or more dyes as well as the operation with different optical configurations of excitation and/or emission wavelengths, in order to image the stained sample at various colors or fluorescence spectra.

In order to image the stained sample at various colors or fluorescence spectra, changes in excitation may be achieved by switching the color of illumination. This can be done, for example, by providing two or more light sources (e.g. for AO, UV LED light at 365 nm and blue LED light at 475 nm) and combining them optically (for example, using a dichroic mirror or grating).

In another example, a single illumination source (e.g. UV LED light at 365 nm) may be used to excite two dyes simultaneously, and one or more optical filters are moved in or out of the optical path to select the relevant emission wavelengths. Other dye sets can be simultaneously excited using the same incident illumination as described here, even if one or more of the dye is excited non-optimally. As an example, AO can be similarly co-excited together with a Hoechst stain, DAPI and DRAQ stains.

In yet another example, a single illumination source (e.g. LTV LED light at 365 nm) may be used to excite two or more dyes simultaneously, and the emission optical path is split such that the two or more emissions are captured on two or more image capturing components.

In yet another example, a color imaging sensor is used to simultaneously capture two or more fluoresce signals. Use of a color imaging sensor can, for example, obviate the need for one or more optical filters that are moved in or out of the optical path to select the relevant wavelength.

In the context of the present disclosure various illumination sources may be used, these include, without being limited thereto, those providing white light (as in bright light microscopy), UV light, blue light, green light, yellow light, red light, combination thereof, or any light applicable for exciting one or more of the dyes used for staining.

The components of the system, namely, the image capturing component, the processing unit, the output unit etc. may be directly connected to each other (e.g. directly by a wire) or one or more of the components may be remote from one or more other components. For example, the image capturing device may send data to a processing unit over an intranet or over the Internet, to allow processing at a remote location.

An example of a system which may be used for performing the method of the present disclosure is described in PCT patent application publication No. WO 2012/090198, the content of which is incorporated herein, in its entirety, by reference.

The processing unit is typically operable by running a dedicated program of instructions (e.g. software application) that performs the analysis and storage of incoming data. The software application may be embodied in a program storage device readable by machine, such as a CD or memory disk.

In line with the above, the present invention also provides a program storage device readable by machine, tangibly embodying the program of instructions executable by the machine to perform the method disclosed herein, namely, a method of detecting a pathogen infection in a sample, the method comprising:

staining said fluid sample with two or more dyes, said two or more dyes providing differential staining of at least DNA and at least one other cellular component being different from DNA;

identifying at least a first stained area corresponding predominantly to DNA and at least one other stained area corresponding to the at least one other cellular component;

extracting structural features for the at least a first stained area and the one other stain area, said structural features comprising at least size of at least one of the first and one other stained areas and a location of said first stained area and said one other stained area one with respect to the other;

determining a value or combination of values being indicative of the presence of a pathogen in the sample if said structural features correspond to structural features predetermined as characterizing a pathogen infection.

Yet further, the present disclosure provides a computer program product comprising a computer useable medium having computer readable program code embodied therein for detecting a pathogen infection in a bodily sample bodily sample being stained with two or more dyes, the computer program product comprising:

computer readable program code for causing the computer to identify in a stained object within the bodily sample;

computer readable program code for causing the computer to identify in the stained object at least a first stained area corresponding predominantly to DNA and at least one other stained area corresponding to at least one other cellular component being different from DNA;

computer readable program code for causing the computer to extract structural features for the at least a first stained area and one other stain area, said structural features comprising at least size of at least one of the first and one other stained areas and a location of said first stained area and said one other stained area one with respect to the other;

computer readable program code for causing the computer to determine a value or combination of values being indicative of the presence of a suspected pathogen in the sample if said structural features correspond to structural features predetermined as characterizing a pathogen infection.

Finally, the present disclosure provides a kit comprising:
a first dye predominantly staining DNA;
a second dye for staining at least one other c component being different from DNA;
instructions for use of said first dye and second dye for determining presence of a suspected pathogen in a bodily sample.

In accordance with this aspect, the first and second dye may be provided in a single composition or in a first composition comprising the first dye and a second composition comprising the second dye. The first and second composition each comprising, in addition to the dye, a carrier suitable for use in staining the bodily sample with the respective dyes.

The kit disclosed herein is to be used for performing each of the steps and conditions of the method disclosed herein.

In some embodiments, the first dye comprises a Hoechst dye. In some embodiments, the second dye comprises acridine orange.

In some embodiments, the kit comprises instructions for providing the bodily sample with the first dye and the second dye at a ratio the range of between 50:1 to 1:1.

In some embodiments, the first dye comprises Hoechst dye, specifically Hoechst 33342 and the second dye comprises AO, the concentration of the first dye is in the range between 3 µg/mL and 250 µg/mL; and the concentration of AO is in the range between 0.2 µg/mL and 125 µg/mL.

In some other embodiments, the first dye comprises Hoechst dye, specifically Hoechst 33342 and the second dye comprises AO, the concentration of the Hoechst 33342 is about 10 µg/mL and the concentration of AO is about 1.5 µg/mL.

In some embodiments, the first and second dyes may be combined with a suitable buffer, such as, without being limited thereto one comprising 1% Tris-EDTA buffer, 4.5% DDW and 92.5% saline.

Without wishing to be bound by theory, it is possible that the AO/Hoechst staining provided more robust and stable staining which enabled rapid and efficient machine vision of the dyed sample. This allowed imaging of a greater amount of blood than may be examined under a microscope in conventional methods, which in turn provided higher sensitivity at low parasitemia. It is also possible (in addition or alternatively) that one or more of the applied criteria of analysis provided dependable results that are not dependent on the human factor Some embodiments of the present disclosure will now be exemplified in the following description of non-limiting examples that were carried out in accordance with the disclosed method. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow.

DESCRIPTION OF SOME NON-LIMITING EXAMPLES

Detection of *Plasmodium* in a Blood Sample

A blood sample obtained from a human subject being identified as having malaria infection was stained with a dye solution comprising 2 µg/ml Acridine Orange, 15 µg/ml Hoechst 33342, 1% Tris-EDTA buffer, 4.5% DDW and 92.5% saline.

After staining, the samples were imaged using different color of illumination, using UV LED light at 365 nm to image AO staining and blue LED light at 475 nm, to image the Hoechst staining). The sample was also imaged in the bright field (illuminating with white light).

Figure 1D:
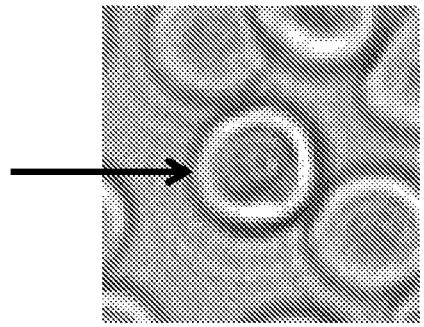
Figure 1B:
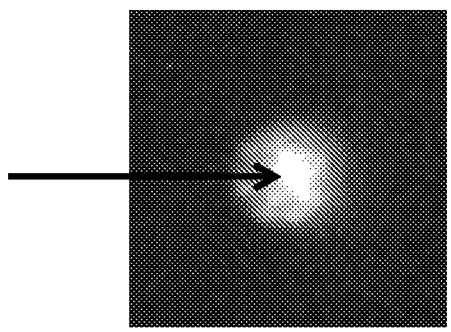
Figure 1E:
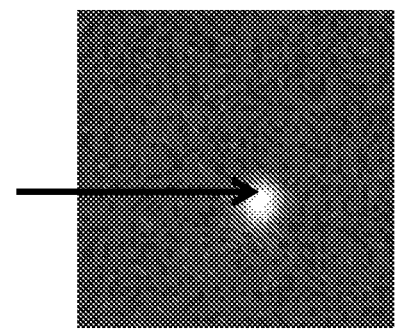
Figure 1C:
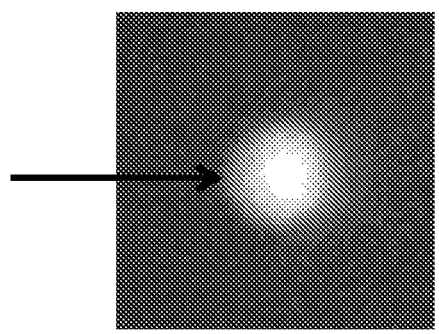
Figure 1F:
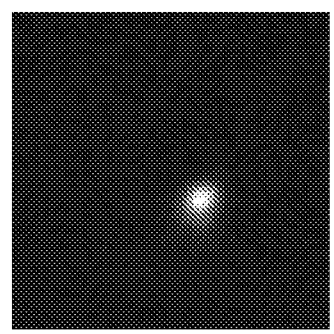

The resulting images are provided in FIG. 1A-1F, with FIGS. 1A-1C being obtained from a sample of white blood cells, and FIGS. 1D-1F being obtained from the malaria infected red blood sample.

Specifically, FIG. 1A shows in the bright light field image, which shows the boundaries (the membrane shown by the arrow in FIG. 1A) of a white cell and that the DNA staining area (arrow in FIG. 1B) and of the other component stained area (in this case the cytoplasm shown by the arrow in FIG. 1C) have dimensions that are typical to a white blood cell (both DNA and RNA staining being larger than typical for a *Plasmodium* parasite).

However, FIGS. 1D-1F show that first stained area (DNA, shown by the arrow FIG. 1E) and the second stained area (RNA, white spot in FIG. 1F) are much smaller than the boundaries of the cell (as shown by the arrow in FIG. 1D), being indicative of an infection of the anucleated red blood cell.

Notably, in a non-infected sample, no stained areas corresponding to those shown in FIG. 1E and FIG. 1F are obtained.

These results show that by staining with at least two dyes, one predominantly staining DNA (in this particular case Hoechst 33342) it is possible to identify *Plasmodium* infection in a red blood cell.

Level of Confidence of Detection

In this study, a group of 200 blood samples was tested in accordance with an embodiment of the present disclosure. Of these blood samples 100 were determined to be positive for malaria using Giemsa stain based on standard microscope methodology and 100 being determined to be negative. A duplicate of each of the 200 samples was stained with a dye solution to have a final concentration in the tested sample of 2 μg/ml Acridine Orange and 15 μg/ml Hoechst 33342 and then analyzed using automated machine vision under bright field, UV light and blue light, essentially as described above. The results showed that more than 97% of the samples that were identified as infected under the conventional method were also identified as such using the AO/Hoechst stain. Out of the 100 samples that were deemed healthy using the conventional Giemsa stain, 93 were confirmed using the AO/Hoechst stain, but seven samples were identified as infected. These seven were then once again analyzed using Giemsa reagent (either by repeating both staining and microscopy with a new sample from the same donor or by further microscopy of the original preparation which gave rise to the negative result). In all seven cases it was confirmed that indeed they were infected, but apparently at a low parasitemia of under 1,000 parasites/μl.

The above shows that not only the method disclosed herein allows detection even by machine vision) of infection with high level of confidence (above 97%), but also when parasite count is very low (low parasitemia), even under 1,000 parasites per μl, or under 500 parasites per μl and even at 20 parasites/μl.

The invention claimed is:

1. A method for identifying a white blood cell within a blood sample, the method comprising:
    staining the blood sample with at least a first dye that predominantly stains DNA, and a second dye that stains at least one other cellular component being different from DNA;
    using a microscope, acquiring a plurality of images of the blood sample, at least one first one of the images being acquired while the blood sample is illuminated under brightfield conditions, at least one second one of the images being acquired while the blood sample is illuminated by a light source having an illumination wavelength that causes the first dye to fluoresce, and at least one third one of the images being acquired while the blood sample is illuminated by a light source having an illumination wavelength that causes the second dye to fluoresce; and
    using at least one computer processor, identifying the white blood cell within the blood sample, by:
        identifying an object within the plurality of images as being a white blood cell candidate, by analyzing the first one of the images;
        identifying that a first stained area, which is stained by the first dye, is disposed within the white blood cell candidate, by analyzing the second one of the images;
        identifying that a second stained area, which is stained by the second dye, is disposed within the white blood cell candidate, by analyzing the third one of the images; and
        determining that one or more structural features of the first and second stained areas satisfy predetermined criteria associated with a white blood cell, the structural features comprising the sizes of the first and second stained area relative to a size of the identified object.

2. The method according to claim 1, wherein identifying the white blood cell comprises distinguishing between the white blood cell and a pathogen.

3. The method according to claim 1, wherein identifying the white blood cell comprises determining that sizes of the first and second stained areas are similar to that of the identified object.

4. The method according to claim 1, wherein identifying the white blood cell comprises determining that sizes of the first and second stained areas are not substantially smaller than that of the identified object.

5. The method according to claim 1, wherein staining the blood sample with the second dye comprises staining the blood sample with Acridine Orange.

* * * * *